(12) United States Patent
Akay

(10) Patent No.: US 7,981,058 B2
(45) Date of Patent: Jul. 19, 2011

(54) INTELLIGENT WEARABLE MONITOR SYSTEMS AND METHODS

(75) Inventor: Metin Akay, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 901 days.

(21) Appl. No.: 11/079,496

(22) Filed: Mar. 14, 2005

(65) Prior Publication Data

US 2005/0240086 A1    Oct. 27, 2005

Related U.S. Application Data

(60) Provisional application No. 60/552,600, filed on Mar. 12, 2004, provisional application No. 60/558,847, filed on Apr. 2, 2004.

(51) Int. Cl.
    *A61B 5/03* (2006.01)
(52) U.S. Cl. .................................................. 600/595
(58) Field of Classification Search .............. 600/587, 600/595, 300
    See application file for complete search history.

(56) References Cited

U.S. PATENT DOCUMENTS 6,165,143 A * 12/2000 van Lummel ............. 600/595
6,307,481 B1 * 10/2001 Lehrman et al. ........... 340/669
6,898,550 B1 * 5/2005 Blackadar et al. ......... 702/182

OTHER PUBLICATIONS

Sekine et al., Discrimination of Walking Patterns Using Wavelet-Based Fractal Analysis, Sep. 2002, IEEE Transactions on Neural Systems and Rehabilitation Engineering vol. 10, 188-196.*
Peng et al., http://reylab.bidmc.harvard.edu/tutorial/DFA/master.html, Alterations in Fractal Dynamics with Aging and Disease,1999, pp. 1-4.*
http://www.m-w.com/cgi-bin/dictionary.*
Rohrer, Brandon et al. "Movement Smoothness Changes during Stroke Recovery", Sep. 15, 2002, The Journal of Neuroscience pp. 4-8.*
Balasubramaniam, Ramesh, "Specificity of postural sway to the demands of a precision task" Oct. 25, 1999, elsevier.com, pp. 4-7.*
Veltink et al. "Detection of Static and Dynamic Activities Using Uniaxial Accelerometers", IEEE Transactions on Rehabilitation Engineering vol. 4. Dec. 1996, 375-383.*
Ling "Activity Recognition from User-Annotated Acceleration Data" 2004. pp. 1-17.*
Jose. "Effects of Parkinson's disease on visuomotor" Exp. Brain Res Mar. 13, 2003 p. 25-29.*
Morrison et al. "Inter and intra-limb coordination in arm tremor" Exp Brain Res (1996) 455-464.*
Keijsers et al. "Automatic Assessment of Levodopa-Induced Dyskinesias in Daily Life be Neural Networks" Movement Disorders 2003 p. 70-80.*

* cited by examiner

*Primary Examiner* — Max Hindenburg
*Assistant Examiner* — Renee Danega
(74) *Attorney, Agent, or Firm* — Lathrop & Gage LLP

(57) ABSTRACT

An intelligent wearable monitoring system includes a wireless personal area network for extended monitoring of a patient's motor functions. The wireless personal area network includes an intelligent accelerometer unit, a personal server and a remote access unit. The intelligent accelerometer unit measures acceleration data of the patient, in real-time. The personal server processes the acceleration data, applying linear and non-linear analysis, such as fractal analysis, to generate motor function information from the acceleration data. Motor function information is transmitted to a remote access unit for statistical analysis and formatting into visual representations. A data management unit receives the formatted motor function information and displays the information, for example, for viewing by the patient's physician.

16 Claims, 16 Drawing Sheets

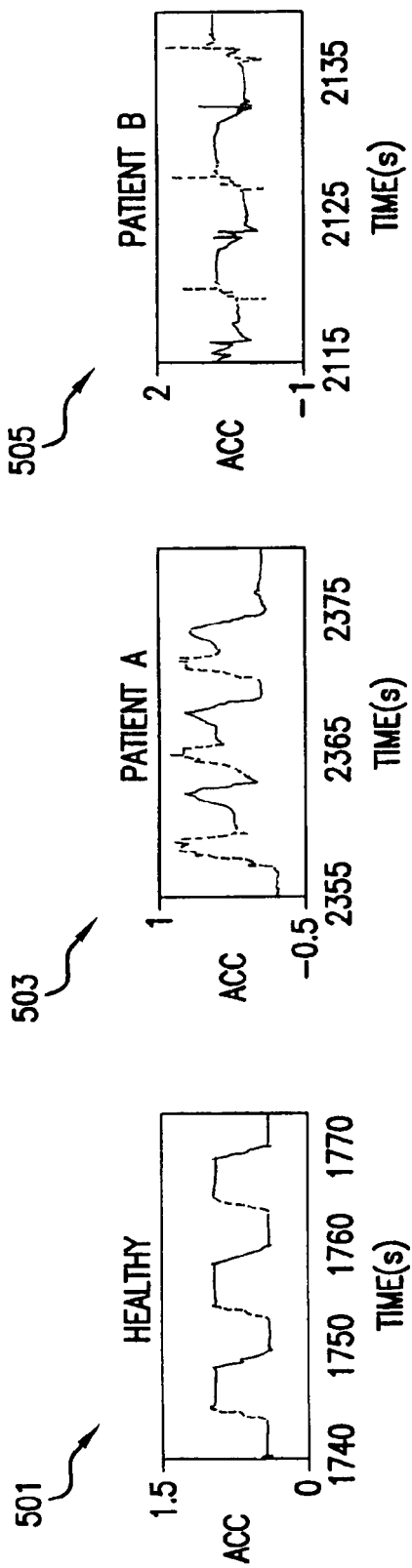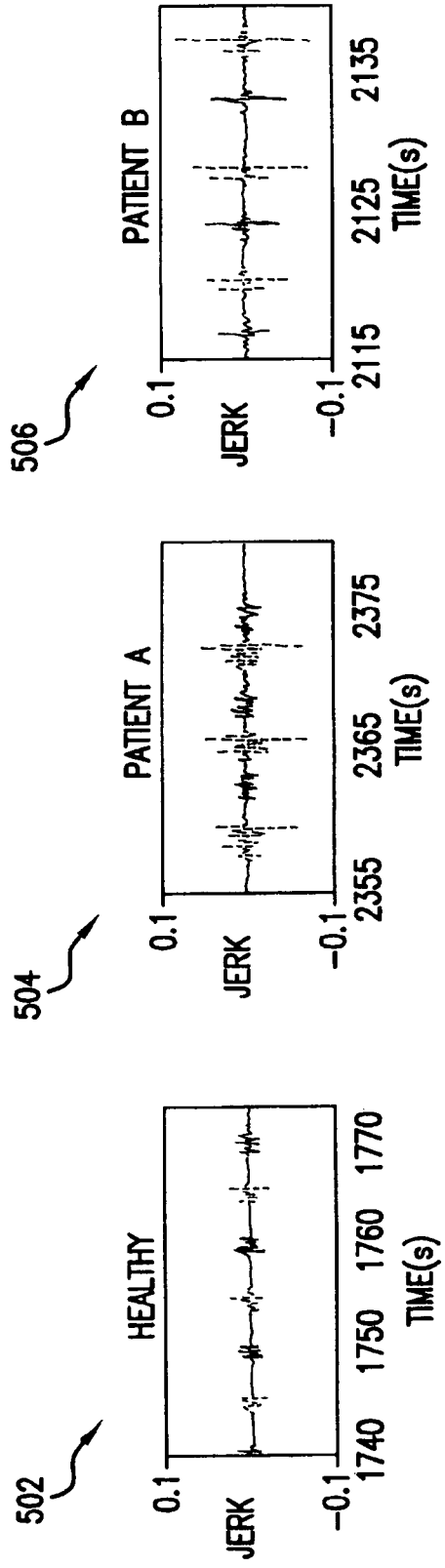

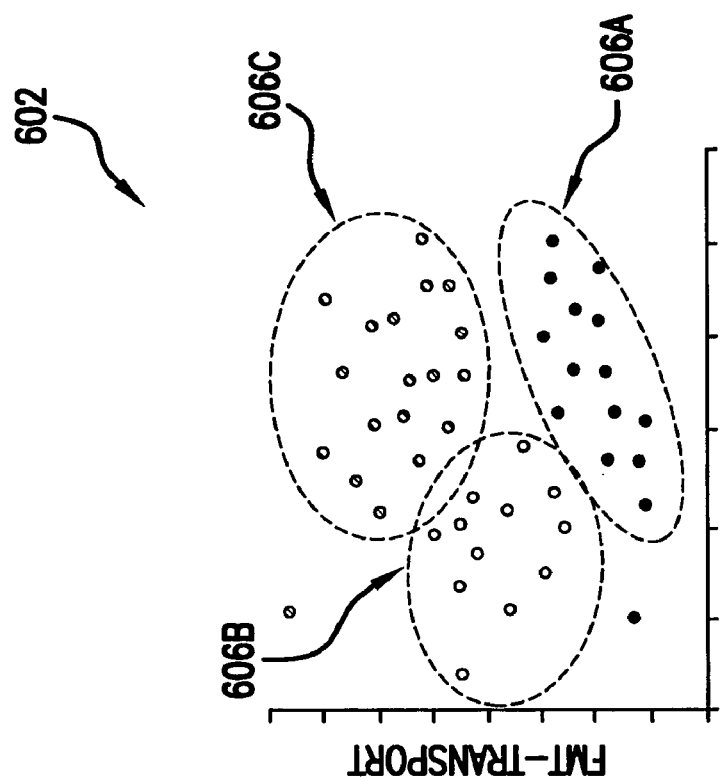
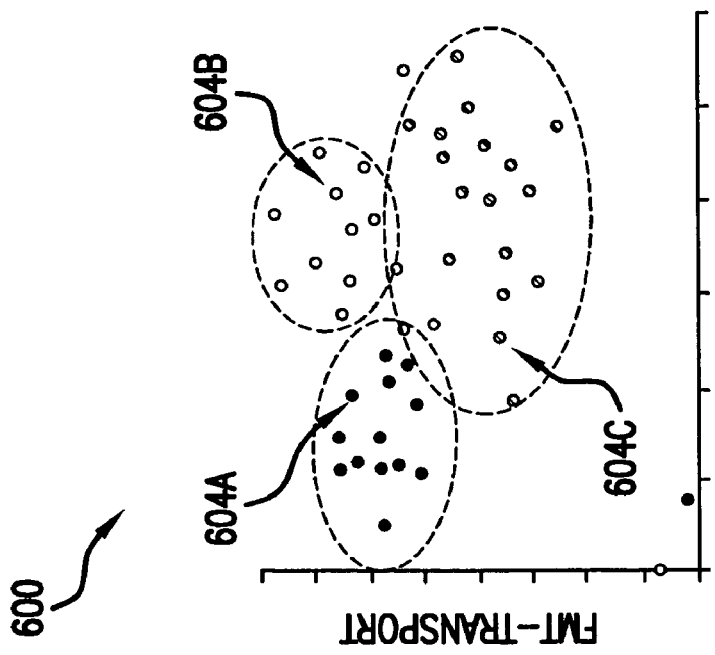
FIG.6B
FIG.6A

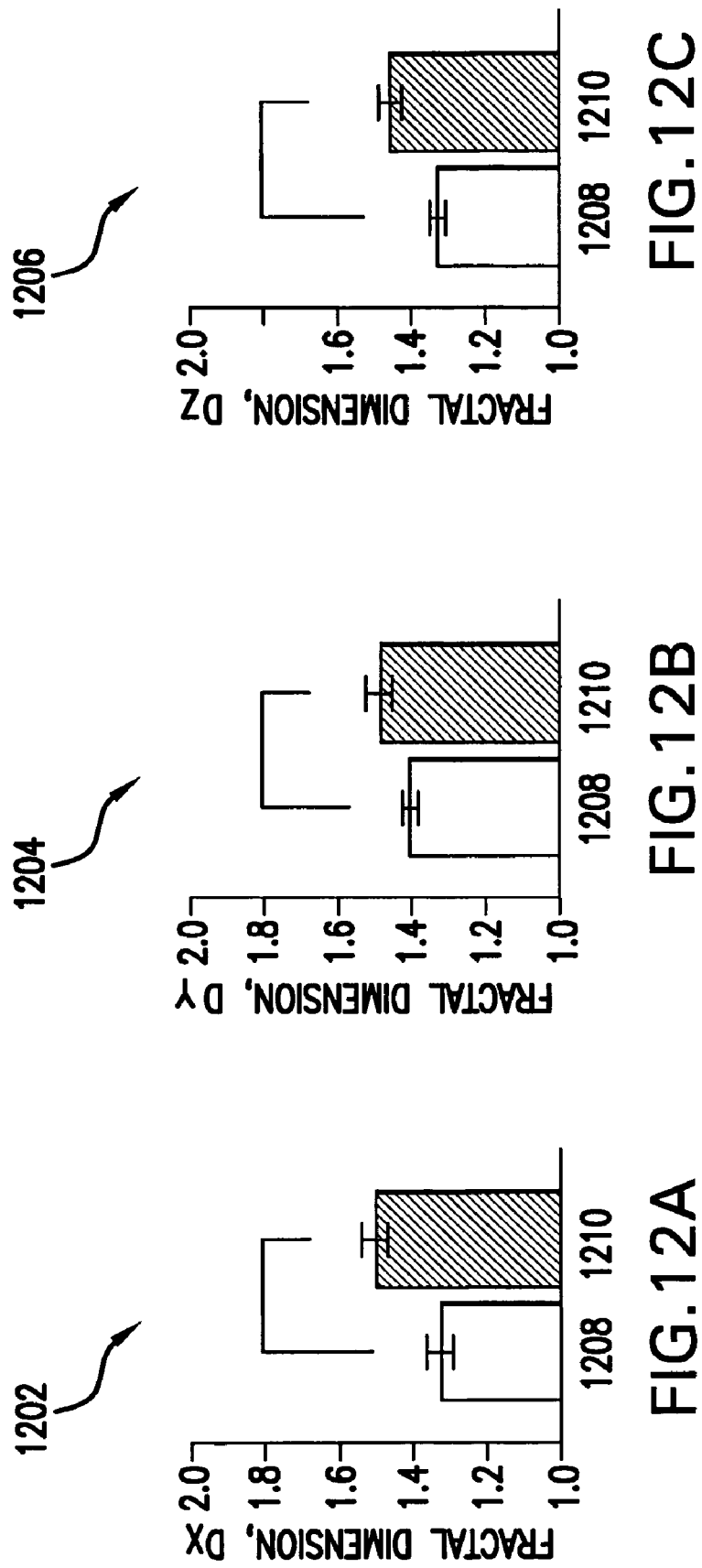

INTELLIGENT WEARABLE MONITOR SYSTEMS AND METHODS

RELATED APPLICATIONS

This application claims priority to (a) U.S. Provisional Patent Application No. 60/552,600, filed 12 Mar. 2004 and entitled PARKINSON'S DISEASE DIAGNOSIS BY FRACTAL ANALYSIS OF BODY MOTION, and to (b) U.S. Provisional Patent Application No. 60/558,847, filed 2 Apr. 2004 and entitled INTELLIGENT WEARABLE MONITOR SYSTEM FOR MONITORING MOTOR FUNCTIONS; both the previous applications are incorporated herein by reference.

STATEMENT REGARDING FEDERALLY SPONSORED RESEARCH

The United States Government has certain rights in this invention pursuant to contract number R01-HL065732 awarded by the National Institute of Health.

BACKGROUND

Parkinson's disease is a disorder which affects brain nerve cells (neurons) that control muscle movement. Accordingly, people with Parkinson's often have difficulty walking or maintaining motor motions (without trembling). Stroke victims also experience difficult or limited movement, on one or both sides of the body.

Although therapy for Parkinson's and post-stroke symptoms is available, researchers still rely on patient observation (for example by studying patient gait) to quantify problems suffered by the patient. Treatment for Parkinson's in any particular patient is therefore still an iterative process involving trial and error.

SUMMARY

As described herein below, systems and methods are disclosed that may improve a patient's quality of life by "fine tuning" the treatment of Parkinson's disease and stroke (and other diseases affecting motor functions). In one embodiment, a patient's body movement is monitored and recorded (typically in three-dimensions) and then geometrically analyzed (for example, with fractal analysis) to determine irregularities.

In one embodiment, an intelligent wearable monitor system includes a wireless personal area network ("WPAN") and a data management unit communicatively connected to the WPAN. The WPAN includes one or more wearable intelligent accelerometer units ("IAU"), a personal server ("PSE") communicatively connected to the WPAN, and a remote access unit ("RAU") communicatively connected to the PSE. The IAU records and preprocesses acceleration data. The PSE processes acceleration data from the wearable IAUs to generate motor function information. The RAU receives the motor function information from the IAU. The data management unit receives, stores and/or displays the motor function information.

In another embodiment, an intelligent wearable monitor system has a WPAN and a data management unit. The WPAN includes one or more IAUs with communicatively connected accelerometers. The IAUs record and process acceleration data measured by the accelerometers. Data is transmitted via a wireless connection to a PSE. The PSE processes the acceleration data to identify and measure motor function(s). Motor function measurements are transmitted from the PSE to a RAU via a second wireless connection. The RAU formats the motor function information. A third wireless connection transmits the motor function information and the formatted information to the data management unit. The motor function and formatted information are displayed at the data management unit.

In another embodiment, a method monitors the motor function of a patient. A patient is fitted with wearable IAUs. Acceleration data is wirelessly recorded via one or more accelerometers of the IAUs, pre-processed, and then transmitted, over a wireless link, and processed into motor function information. The motor function information is then transmitted to a RAU via a second wireless link, and, if desired, formatted. The formatted motor function information is then wirelessly transmitted to a data management unit, and viewed to determine a level of functional impairment of the patient.

In another embodiment, a method monitors the motor function of a patient and includes the steps of: fitting the patient with a wearable monitoring system; wirelessly recording first acceleration data of the patient with one or more accelerometers; pre-processing the first acceleration data; transmitting the acceleration data over a wireless link to a server; dividing the acceleration data into first epochs; training an artificial neural network with the first epochs; processing the first acceleration data into movement information; dividing the movement information into second epochs; marking the second epochs with an electronic marker; training the artificial neural network with the second epochs; analyzing the first and second epochs with the artificial neural network to generate motor function data; wirelessly transmitting motor function data to a remote access unit; wirelessly transmitting motor function data to a data management unit; and viewing the data to assess a level of the motor function.

BRIEF DESCRIPTION OF DRAWINGS

FIGS. 5A-5F depict exemplary graphical output of the remote access unit.

FIGS. 6A-6B show exemplary Sammon projections such as generated by the remote access unit.

FIGS. 12A-C depict three bar graphs showing differences in the mean value and standard deviation of fractal dimensions measured for a Parkinson's patient and a healthy elderly subject.

DETAILED DESCRIPTION OF DRAWINGS

Figure 1:
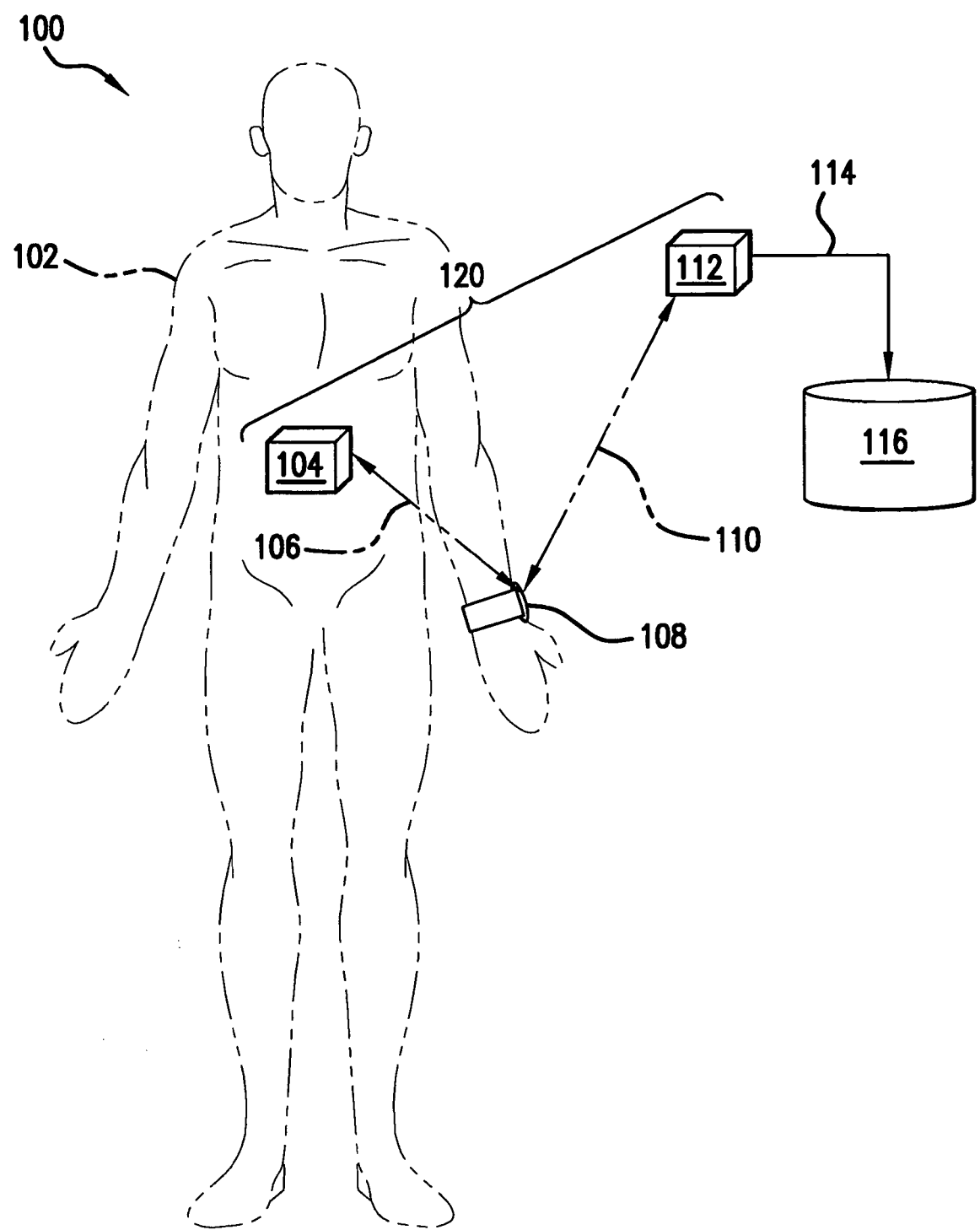
FIG. 1 shows one intelligent wearable monitor system embodiment.

FIG. 1 shows an embodiment of an intelligent wearable monitor system 100. A wearer example patient 102, wears an intelligent accelerometer unit ("IAU") 104, which records acceleration data with acceleration sensors/accelerometers (i.e., accelerometers 204$x$, 204$y$, FIG. 2), pre-processes the acceleration data and transmits the acceleration data over wireless link 106 to a personal server ("PSE") 108, also worn by patient 102. Accelerometers 204$x$, 204$y$ are for example, ADXL202E accelerometers by Analog Devices. Each IAU may include pulse width modulation ("PWM") converters (not shown) associated with each acceleration channel. IAU 104 may also be calibrated to adjust channel sensitivity and offset parameters of the accelerometers and PWM converters.

PSE 108 may be configured as a watch or bracelet including a digital signal processor, one or more displays and/or audio speakers to confirm operational status of system 100 (i.e., to show whether PSE 108, IAU 104 and/or a remote access unit ("RAU") 112 are for example turned on, turned off, currently busy, or not working). PSE 108 may also have input capability (e.g., buttons) allowing patient 102 to turn PSE 108 on or off. In one embodiment, PSE 108 is also configured for remote operation of IAU 104 (e.g., PSE 108 transmits control signals to IAU 104 to turn IAU 104 on or off, or to initiate data transfer from IAU 104 to PSE 108). PSE 108 may further include peripheral modules and optic/acoustic signals that confirm the transmission of data.

PSE 108 processes acceleration data to generate motor function information and sends the motor function information, via wireless link 110 (e.g., an Ethernet or wireless link, such as Bluetooth), to RAU 112. Motor function information may include, but is not limited to, identification of a physical activity, quality of movement ("QOM") measurements, smoothness measurements, complexity measurements, linear measurements, non-linear measurements and fractal data. Hereinafter, the terms "motor function information" and "movement information" are used interchangeably. In one embodiment, PSE 108 controls the operation of RAU 112, for example, turning RAU 112 on or off.

RAU 112 is preferably a personal digital assistant, but may be a personal computer, a cellular telephone or another wireless device in possession of the patient (or, optionally, in possession of the patient's physician). When RAU 112 is in possession of a patient at home or in the community, link 110 is for example a Bluetooth link with a range of at least 15 m. Collectively, IAU 104, PSE 108 and RAU 112 may be referred to as wireless personal area network (WPAN) 120. WPAN 120 may provide a hierarchical and distributed signal processing architecture, providing adaptability of the system to a particular individual or therapeutic application.

In one embodiment, RAU 112 of WPAN 120 connects with a data management unit 116 over a link 114. Link 114 may be, for example, a public switched telephone network ("PSTN"), a fully wireless link, an additional WPAN client with a serial link to a cellular telephone, or an Internet connection, for example.

Data management unit 116 may, for example, be a personal computer located in a medical center, physician's office or other clinical location. PSE 108, RAU 112 and data management unit 116 may each include one or more displays for displaying the movement information, time, date and/or other desirable information.

Figure 2:
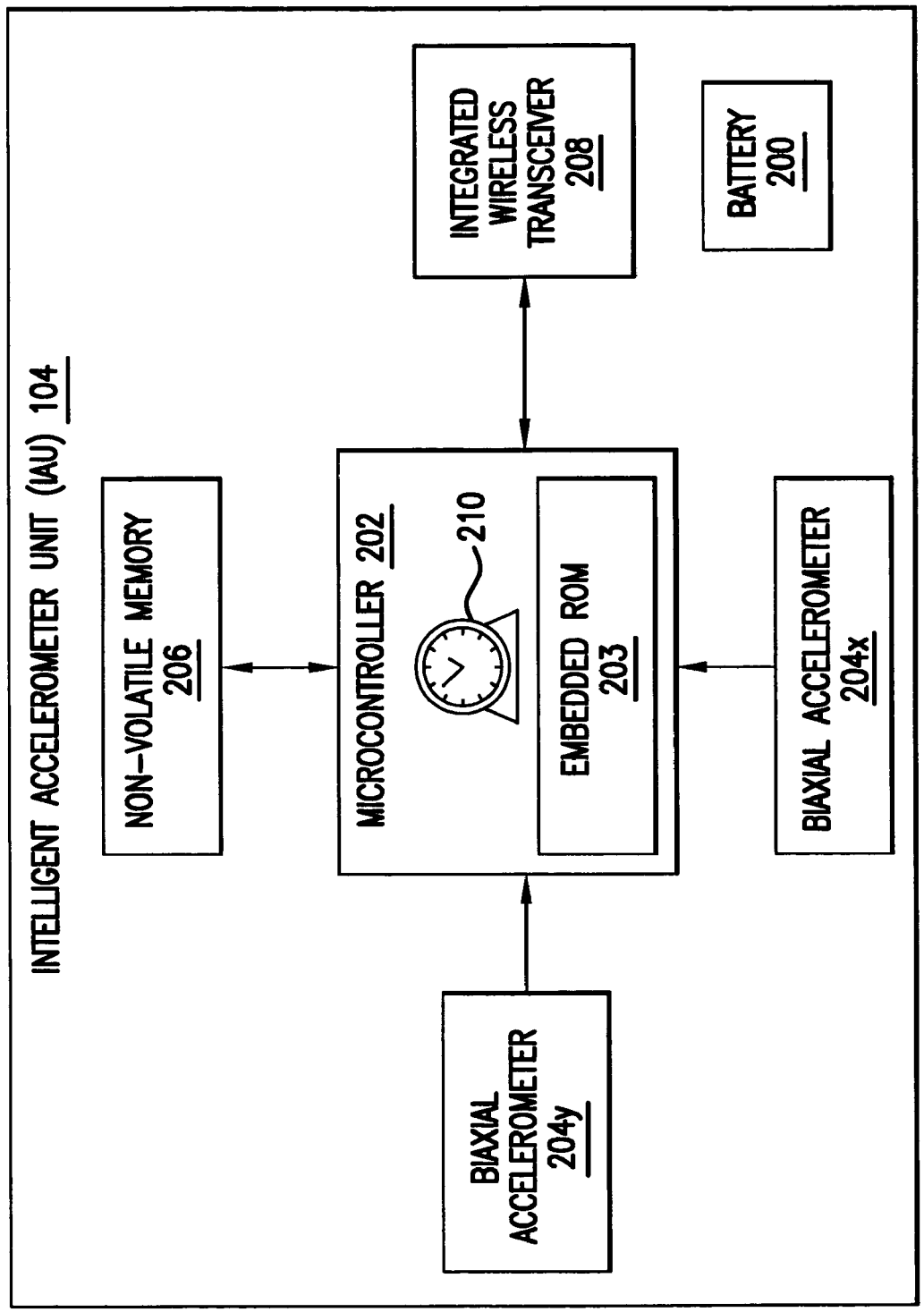
FIG. 2 shows a block diagram of one intelligent accelerometer unit of the intelligent wearable monitor system of FIG. 1.

Intelligent wearable monitor system 100 may be configured to (1) monitor motor functions of a patient in real-time and over a time span (e.g., one week, or more, or less) and (2) process accelerometer data to identify the occurrence of motor functions, determine the nature of the activities and assess the QOM associated with the motor functions. As shown in FIG. 2, IAU 104 may include a battery 200. Battery 200 may be a rechargeable (e.g., Ni—Cd) or a non-rechargeable battery (e.g., a lithium battery). In one embodiment, the battery 200 allows IAU 104 to operate for over ten days if active 24 hours per day, or for over twenty days if IAU 104 is active only 12 hours per day. Battery 200 may however be configured to operate for over thirty-six hours with an average current of about 0.3 mA or less when IAU 104 reverts to a sleep mode between sampling of acceleration. Other embodiments may use rechargeable and/or non-rechargeable batteries over different periods of time, for example, by varying the duration of the sleep mode. For example, when a read cycle of IAU 104 is dominated by sleep mode, IAU 104 may only require an average supply current of 0.67 mA.

In one embodiment, IAU 104 further includes a microcontroller 202, two or more biaxial accelerometers 204$x$ and 204$y$ (e.g., providing four channels of acceleration data), non-volatile memory 206, an integrated wireless transceiver 208, and connections therebetween (power connections of battery 200 are not shown, for clarity of illustration). Accelerometers 204$x$ and 204$y$ are shown as biaxial accelerometers mounted on orthogonal planes x, y and within IAU 104; however, it will be appreciated that alternate configurations may be implemented, including alternate accelerometers (such as uni-axial or tri-axial accelerometers) or additional accelerometers. For example, in one embodiment, IAU 104 includes three bi-axial accelerometers mounted on orthogonal planes, providing six channels of acceleration data. IAU 104 may also include accelerometers physically separated from, but communicatively connected with, IAU 104. For example, IAU 104 may include commercially available MEMS sensors, communicatively connected to IAU 104 and placed upon the patient's body (for example, placed on the hand, forearm, and upper arm to measure fine motor movement such as writing).

In operation, accelerometers 204$x$ and 204$y$ generate acceleration data for microcontroller 202. Microcontroller 202 may include embedded memory, for example, read only memory ("ROM") 203 containing software instructions for execution of microcontroller 202 to perform data acquisition and processing, as discussed below. Microcontroller 202 pre-processes the acceleration data and transfers the acceleration data to and from non-volatile memory 206. Microcontroller 202 may include a clock 210; and a time and date at which microcontroller 202 receives acceleration data may be output with the acceleration data. Microcontroller 202 also interfaces with transceiver 208 to receive and execute requests for measuring acceleration signals, preprocess data and/or transfer data to or from transceiver 208 (for wireless broadcast to PSE 108, for example). Data processing such as identifying movement and analyzing and generating movement information from acceleration data may be performed by PSE 108.

Wearable monitor system 100 may be calibrated to a patient. Calibration includes recording acceleration data from a patient during directed activities, identifying the activity-specific acceleration data generated for each directed activity, and storing the activity-specific acceleration data in a memory. PSE 108 may also process the activity-specific acceleration data to generate activity-specific motor function information. The activity-specific motor information may also be stored in a memory.

Consider for example patient 102 wearing IAU 104 and PSE 108 in a physician's office or other clinical setting. Patient 102 may be directed to perform a variety of activities of daily living ("ADL"), such as: standing from a sitting position; sitting from a supine position; manual tasks such as drinking from a cup, tracing, writing, putting on and buttoning clothing, food cutting, tooth brushing, hair combing; walking; stair climbing; and/or other motion related to an exercise program. Acceleration sensors, for example accelerometers 204x and 204y detect acceleration signals as patient 102 performs these ADL.

Microcontroller 202 of IAU 104 performs preprocessing functions, for example checking the accelerometers, grouping acceleration data and attaching information to the acceleration data, and may temporarily store the acceleration data in non-volatile memory 206. Microcontroller 202 transfers acceleration data from IAU 104 to PSE 108 via wireless transceiver 208.

Figure 3:
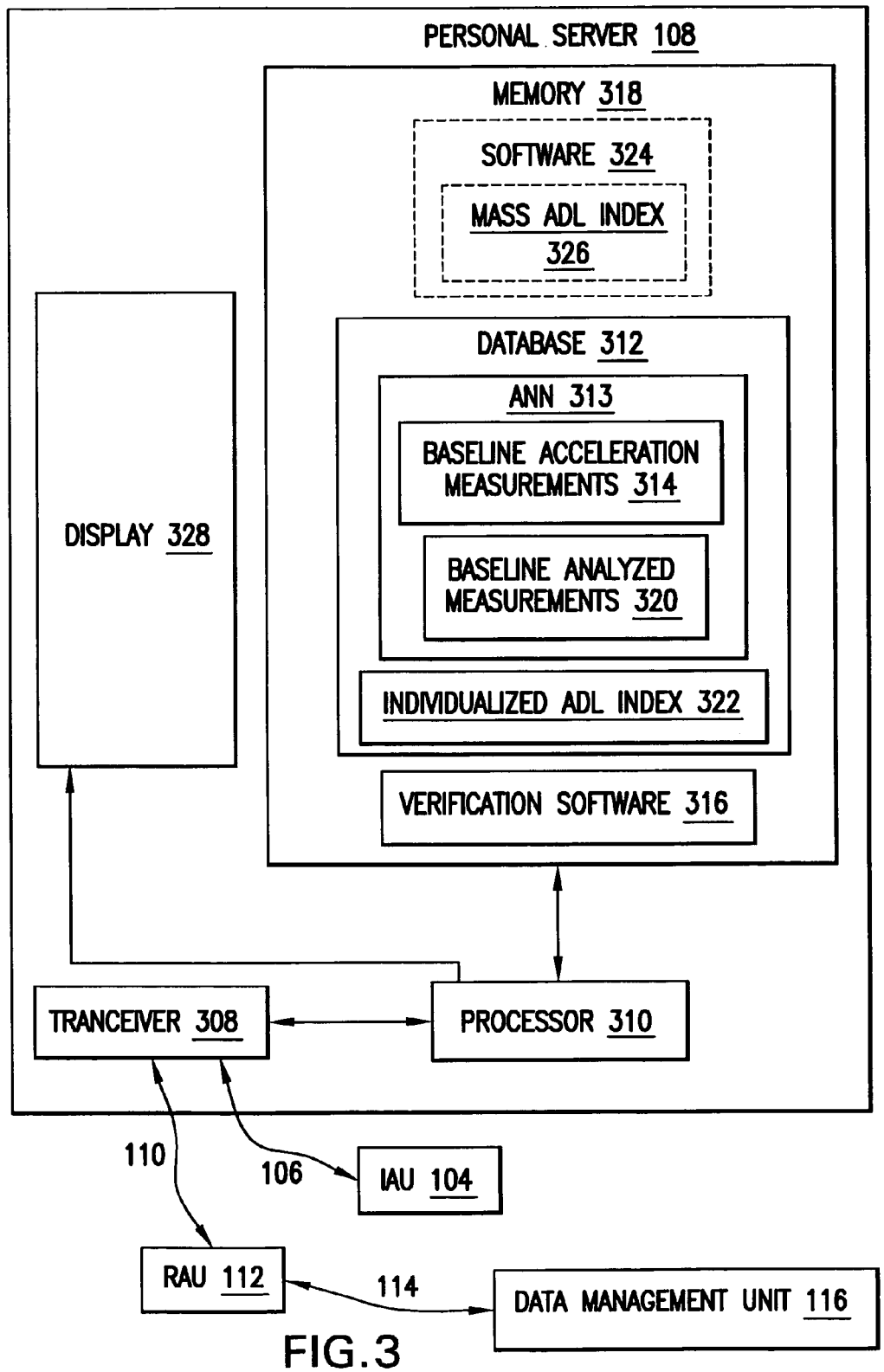
FIG. 3 is a block diagram of one personal server of the intelligent wearable monitor system of FIG. 1.

As shown in the embodiment of FIG. 3, PSE 108 includes a wireless transceiver 308 that transmits and receives data to and from IAU 104, RAU 112 and optionally, data management unit 116. Acceleration data received from IAU 104 and transferred to processor 310 may then be segmented into epochs in order to select time intervals associated with the various ADL. This segmented acceleration data may then be used, for example, to train an artificial neural network ("ANN") 313 of database 312. Segmented acceleration data related to various ADL may be stored within ANN 313 as baseline measurements 314 of motor function, enabling processor 310 to identify occurrences of the ADL based on corresponding segmented acceleration data. For example, processor 310 may identify occurrences of the ADL by comparing new segmented data with baseline measurements 314. Verification software 316 may be included to provide verification of segmentations performed on the basis of an electronic marker, and correction of mistakes occurring at the time of data collection.

Further processing may be performed by processor 310 to separate acceleration data related to gross postural adjustments (e.g., less than 1 HZ) from actual acceleration of body segments (e.g., greater than 1 HZ). Processor 310 may also process the acceleration data into movement information. For example, processor 310 may apply an algorithm to estimate a derivative of the acceleration components as an estimated jerk—the rate of change in the acceleration of an object—and integrate the acceleration to estimate the velocity of displacement of body segments. In an alternate embodiment, concurrently recorded electromyographic ("EMG") data may be used to correlate acceleration data with the ADL.

Processor 310 may compute linear features from the acceleration data and estimated jerk. For example, processor 310 may assess the complexity or quality of movement by computing linear values such as the root mean square ("RMS") value and range of autocorrelation function, calculated separately for high frequency and low frequency acceleration signal components (i.e., above and below one Hz, respectively). For example, the RMS may be computed as a measure of the magnitude of the acceleration signal for a collection of N signal values $\{x_1, x_2, \ldots, x_N\}$ according to the following equation:

$$x_{rms} = \sqrt{\frac{1}{N}\sum_{i=1}^{N} x_i^2} \qquad \text{Eq. 1}$$

$$= \sqrt{\frac{x_1^2 + x_2^2 + \ldots + x_N^2}{N}}.$$

The corresponding formula for a continuous function $f(t)$ defined over the interval $T_1 \leq t \leq T_2$ is:

$$x_{rms} = \sqrt{\frac{1}{T_2 - T_1} \int_{T_1}^{T_2} [f(t)]^2 \, dt}. \qquad \text{Eq. 2}$$

Processor 310 may further calculate correlation coefficients for pairs of acceleration channels, a smoothness metric (i.e., negative mean jerk normalized by peak velocity) and an RMS value of the jerk metric.

PSE 108 may also perform dynamic nonlinear analyses to compute linear features (i.e., fractal dimensions) from the acceleration data, according to an approximate entropy ("AE") method, a maximum likelihood estimator ("MLE") fractal method, approximate cross entropy ("ACE") method, and/or an average amount of mutual information ("AAMI") measures, each are known in the arts of computing and statistical assessment.

The MLE fractal method, for example, is recognized as being asymptotically unbiased and an efficient estimator. To implement the MLE fractal method, the algorithm maximizes the log of the probability density function p(x; H) instead of p(x, H), where x is the input signal and H is the Hurst exponent, as follows:

$$\log p(x; H) = -\frac{N}{2}\log 2\pi - \frac{1}{2}\log|R| - \frac{1}{2}x^T R^{-1} x \qquad \text{Eq. 3}$$

where N is the total number of samples and R represents the covariance matrix. The elements of R are given by:

$$[R]_{ij} = \frac{\sigma^2}{2}[|k+1|^{2H} - 2|k|^{2H} + |k-1|^{2H}] \qquad \text{Eq. 4}$$

where $\sigma^2$ is the variance of signal x[k] for k=[i-j]. The algorithm finds the optimum H value in order to maximize the equation. H is limited to the interval [0,1] for a one-dimensional signal, and is directly related to the fractal dimension D as D=2−H in the range 1<D<2.

The AE algorithm may be computed, for example, as a measure of an irregularity of a patient's movement while executing ADL. The AE algorithm summarizes a time series as a single nonnegative number, with higher AE values representing more irregular systems. The AE algorithm may be particularly suited to the analysis of acceleration data because it is model-independent and quantifies the complexity of a wide, dynamic range of biological signals, including signals that are outputs of complex biological networks. To determine the AE estimates, vector sequences X(i) through X(N−m+1) defined by X(i)=[x(i+m+1)] are for example constructed from given N data points for i=1, N−m+1. The difference between X(i) and X(j), d[X(i), X(j)] as the maximum absolute difference between their related scalar elements is for example estimated as:

$$d[X(i),X(j)] = \max_{k=0,m-1}[|x(i+k)-x(j+k)|] \quad \text{Eq. 5}$$

assuming that all the differences between the corresponding elements will be less than d. For any given X(i), the ratio $C_r^m(i)$ of the number of difference between X(i) and X(j) smaller than a threshold, r, to the total number of vectors (N−M+1) is:

$$C_r^m(i) = \frac{N^m(i)}{(N-m+1)} \text{ for } i = 1, N-m+1 \quad \text{Eq. 6}$$

The approximate entropy, AE(m,r), is then estimated as a function of the parameters m and r as follows:

$$AE(m,r) = \lim_{N \to \infty} \lfloor \phi^m(r) - \phi^{m+1}(r) \rfloor \quad \text{Eq. 7}$$

where $$\phi^m(r) = \frac{1}{(N-m+1)} \sum_{i=1}^{N-m+1} \ln C_r^m(i) \quad \text{Eq. 8}$$

Note that the parameter m is the embedding dimension of the signal and the parameter r is the threshold to suppress the influence of noise. In practice, AE values may be estimated for the signal with N number of samples as $$AE(m,r,N) = \lfloor \phi^m(r) - \phi^{m+1}(r) \rfloor \quad \text{Eq. 9}$$

In one embodiment, m is a user selectable parameter. For example, m may be chosen to be two. The parameter r may also be user selectable, for example taken as 0.1 SD(x(i)), where SD (x(i)) is the standard deviation of the original signal (x)i.

PSE 108 may store the results of analysis of ADL in a memory 318 associated with PSE 108 as processed (e.g., motor function) data. PSE 108 may use the processed data for further training of ANN 313, in the same manner as performed when training ANN 313 with acceleration data. Processed data used in training ANN 313, for example linear and non-linear (i.e., fractal dimensions) data, may be stored within ANN 313 as baseline analyzed (motor function) measurements 320, thus allowing identification of ADL utilizing either or both of processed data and analyzed data. PSE 108 may also store acceleration data and processed data related to repeat performances of the ADL (i.e., those used in calibration) in an individualized ADL index 322 for patient 102. For example, acceleration data related to an ADL may be recorded by IAU 104, along with the time and date of performance, and data therefrom may be processed by PSE 108 for recognition via ANN 313. Once identified, the processed data (e.g., motor function information) may be stored in individualized ADL index 322 and may thus facilitate measurement of changes in patient 102's motor function, in real-time and/or over a time span. Optionally, a mass ADL index 326 of processed data from a number of healthy and movement-compromised patients may be included with software 324, thus allowing a comparison of patient 102's motor function with that of others. For example, patient 102's motor function information may be compared to motor function information of patients affected by neurological disorders, as a diagnostic tool. Mass ADL index 326 may also allow for assessment of patient 102, for example, on a scale of compromised-to-uncompromised motor function.

Optionally, data management unit 118 may also include the mass ADL index and may retain and augment the ADL index for patient 102, for example as a back-up measure or to create a comprehensive ADL index for all patients of a particular physician or medical group who are utilizing an intelligent wearable monitor system 100.

Figure 4:
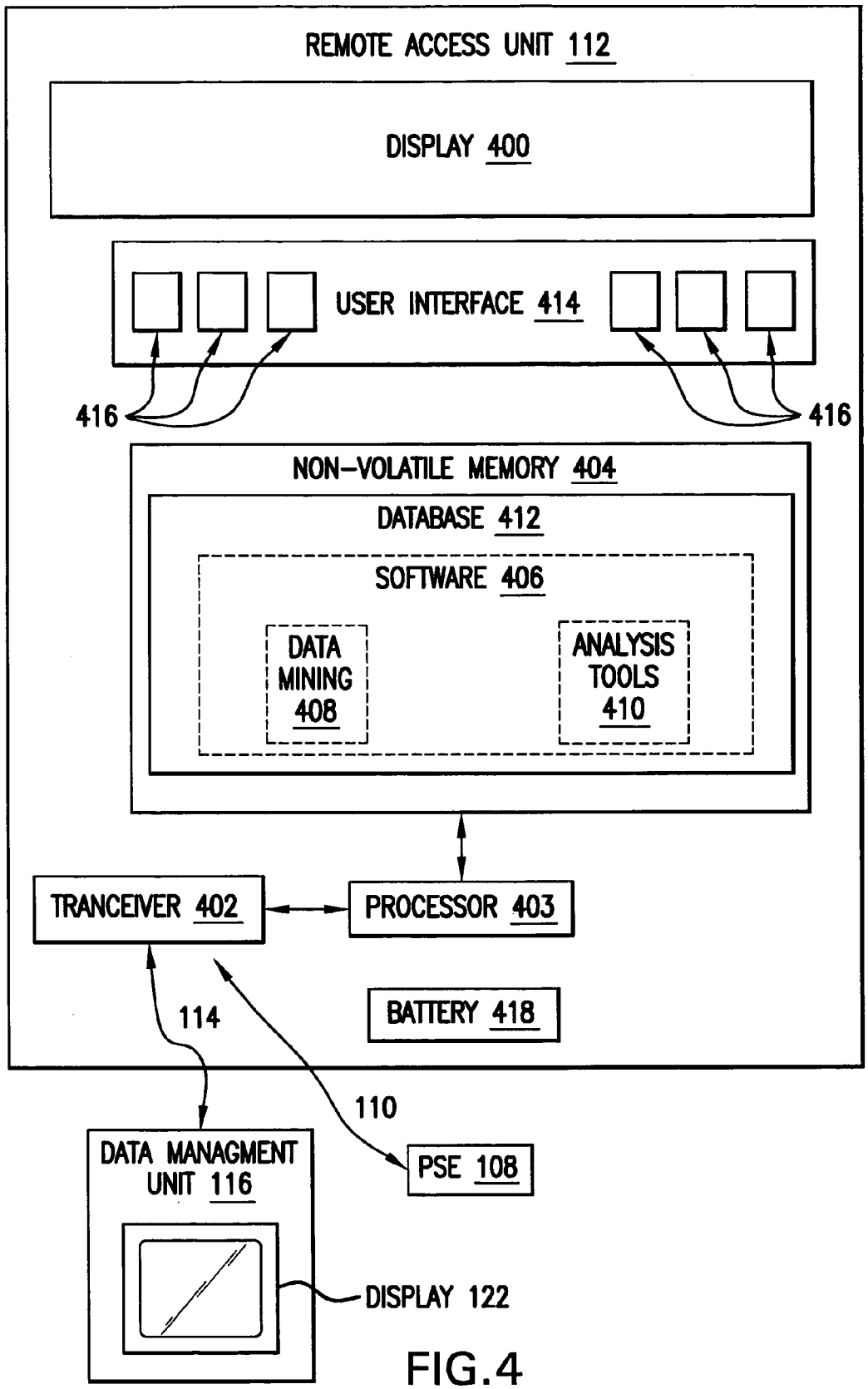
FIG. 4 is a block diagram showing one remote access unit of the intelligent wearable monitor system of FIG. 1.

PSE 108 may also include a battery (not shown) and at least one display 328 that displays motor function information and/or other useful information, such as time and date. The analyzed movement information may also be sent to RAU 112 via transceiver 308 and wireless link 110, where it may also be viewed and transferred via wireless link 114 to data management unit 116 (where it is additionally viewable at display 120, as shown in FIG. 4). In one embodiment, RAU 112 formats the motor function information and transfers the formatted information and/or the motor function information to data management unit 116. Formatting, as used herein, includes but is not limited to performing statistical analysis and/or data mining.

FIG. 4 shows RAU 112 of intelligent wearable monitor system 110. RAU 112 includes display 400, transceiver 402 for receiving and sending communications to and from PSE 108 and data management unit 116 via links 110 and 114, respectively. RAU 112 also includes processor 403, non-volatile memory 404, database 412, battery 418 and connections therebetween (for ease of illustration, battery connections are not shown). Upon instruction received from a user at user interface 414, for example, via user keys 416, processor 403 may initiate formatting, for example, by initiating data mining 408—a collection of tools designed to explore data sets (e.g., motor function information) to search for consistent patterns and systematic relationships among variables. Data mining 408 may be performed by execution of software 406 stored in database 412. Software 406 may also provide statistical analysis tools 410 for performing statistical analysis of the motor function information. Data mining 408 may first be implemented to provide a reduction in feature space dimensionality before utilizing analysis tools 410. Data mining 408 may also be used to generate statistics and visual representations such as tables, charts, bar and other graphs, histograms, brushing and graphical summaries. These visual representations (e.g., as shown in FIGS. 5A-F and 6A-B, below) may be viewed at display 400. The formatted information (e.g., statistics and visual representations) may also be automatically transmitted to data management unit 116 via transceiver 402 over link 114. Optionally, RAU 112 may save data, including the formatted information, in non-volatile memory 404 for uploading to data management unit 116. This capability may guard against loss of data, for example in the event of battery or connection failure.

FIGS. 5A-5F and 6A-6B show exemplary visual representations, for example, as generated by RAU 114 from movement information provided by PSE 108 (see Results herein below for further description of physical activities behind the measured movement information). It is to be understood and appreciated that output, or formatted information, of RAU 114 may also take alternate forms, such as recited herein above. For example, principal components analysis ("PCA") may be applied by PSE 108 to reduce acceleration data of an ADL to its principal components. RAU 114 may plot the principal components for comparison to principal components from other patients, or control subjects, to corroborate the ADL identified by PSE 108. The use of PCA may enable, for example, classification of activities for which ANN training data is unavailable. PCA analysis may be performed, for example, as per the methods described in "Principal Components Analysis," Joliffe, I. T., New York: Springer-Verlag, 1986, incorporated herein by reference.

More particularly, FIGS. 5-C show graphic representations 501, 503 and 505 of acceleration data as generated by a healthy elderly ("HE") subject, a motion-impaired patient A and a motion-impaired patient B, respectively, during the task of moving the hand from lap to table. Acceleration data is shown in units of gravity–g≅9.8 m/s² of the forearm along an axis oriented perpendicular to the skin surface. FIGS. 5D-5F show graphic representations 502, 504 and 506 of jerk computed from the acceleration data generated by the HE subject, patient A and patient B, respectively. FIGS. 5D-5F show jerk normalized by peak velocity (s⁻²) as computed from the acceleration data.

Motion-impaired patient A (FIGS. 5B and 5E) was assessed with a Fugl-Meyer score of 31 and a Motor function Log (MAL) score of 0.9. Patient B (FIGS. 5C and 5F) was assessed with a Fugl-Meyer score of 50 and a MAL score of 1.8. Segments (i.e., successive repetitions of the same task) that were used for analysis by PSE 108 are represented by dotted portions of the graphic representations 501-506. FIGS. 5A-5F demonstrate, for example, that information distinguishing subjects with different levels of motion impairment is present in the linear features computed from the acceleration data.

FIGS. 6A-6B depict Sammon projections 600 and 602, respectively. Sammons projections 600 and 602 show non-linear feature sets 604A-604C and linear feature sets 606A-606C, respectively, computed by PSE 108 from acceleration data recorded by IAU 104 during functional motor tasks ("FMT"), i.e., transport. The FMT included forearm-to-table, forearm-to-box, hand-to-table and hand-to-box tasks (see Results herein below, for a complete listing of performed FMT). Data sets 604A and 606A are represented by dotted lines encircling a cluster of solid-dot data points generated for a healthy elderly subject performing the FMT. Data sets 604B and 606B are represented by dotted lines encircling a cluster of open-dot data points generated for patient A (i.e., patient A of FIG. 4). Data sets 604C and 606C are represented by dotted lines encircling a cluster of hatched-dot data points, generated for patient B (i.e., patient B of FIG. 4).

FIGS. 6A and 6B demonstrate, for example, the capability of PSE 108 to apply both linear (FIG. 6A) and nonlinear (FIG. 6B) analysis to acceleration data, to produce motor function information that is different for subjects with different levels of motion impairment. There are no units on the x, y axes of FIGS. 6A-6B because the Sammons projections are two-dimensional and occupy a domain defined by arbitrary axes that do not lend themselves to a direct physical interpretation.

An intelligent wearable monitor system may also provide for enhanced assessment and monitoring of post-stroke patients. Stroke victims often experience hemiparesis—paralysis or weakness affecting one side of the body. Recently, movement therapies such as body weight support treadmill training, intensive upper limb exercise, functional electrical stimulation, robotic therapy and constraint-induced movement therapy (CIT) have demonstrated that motor recovery is possible even several years after stroke onset.

In one embodiment, the present system and related methods provide qualitative measurement of QOM, and long-term assessment of functional limitations in stroke patients. The QOM data gathered and output by intelligent wearable monitor system 100 may substitute for or a complement to conventional assessment measures such as the Wolf Motor Test, the MAL and the Actual Amount of Use test, each of which is known in the art.

Figure 7A:
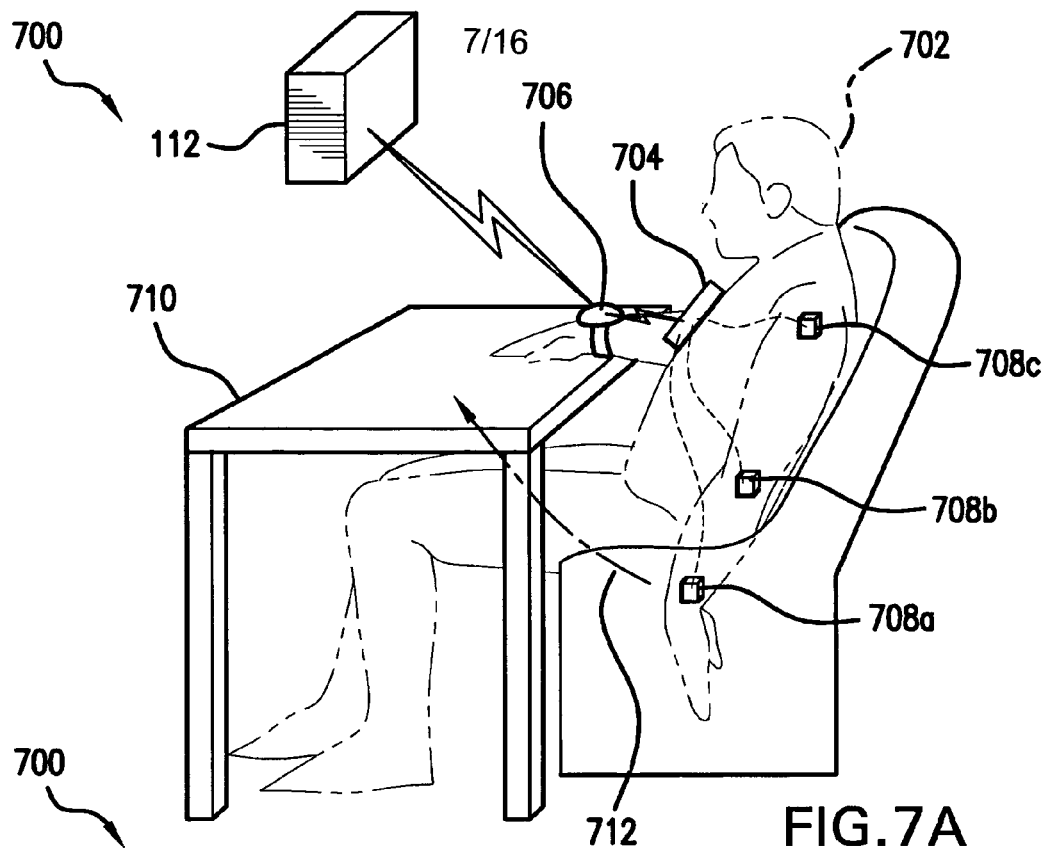
FIGS. 7A-B depict an application of an intelligent wearable monitor system in measuring and assessing movement, in accordance with an embodiment.
Figure 7B:
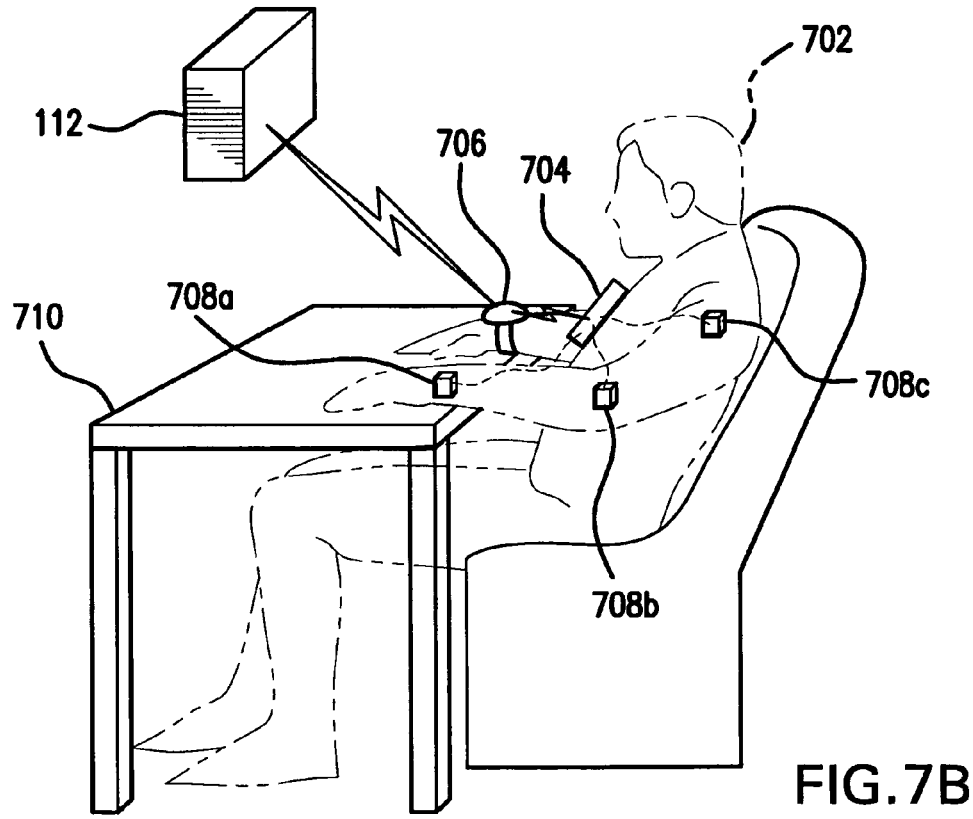

FIGS. 7A-B show an intelligent wearable monitor system 700. As previously described, a patient, e.g., patient 702 wears an IAU 704 and a PSE 706. In the embodiment of FIG. 7A, three bi-axial accelerometers 708a, 708b and 708c are applied to the back of the hand and the lateral aspect of the lower and upper arm on the affected side of the body as patient 702 performs a task of the Wolf Motor Function test, for example, moving an arm from the side, in the direction of movement arrow 712 (FIG. 7A), to rest upon a table 710, as shown in FIG. 7B. Accelerometers 708a-c are communicatively connected to IAU 704. Accelerometers 708a-c need not replace the accelerometers integrated with IAU 704 (i.e., accelerometers 204x and 204y of FIG. 2), but may serve as an aid in initially identifying the acceleration data correlating to fine motor movements. In one embodiment, bi-axial accelerometers 708a, 708b and 708c may correlate acceleration data measured by accelerometers within IAU 104 (i.e., accelerometers 204x and 204y) during calibration in a clinical setting. Accelerometers 708a-c may be unnecessary after calibration.

Figure 8A:
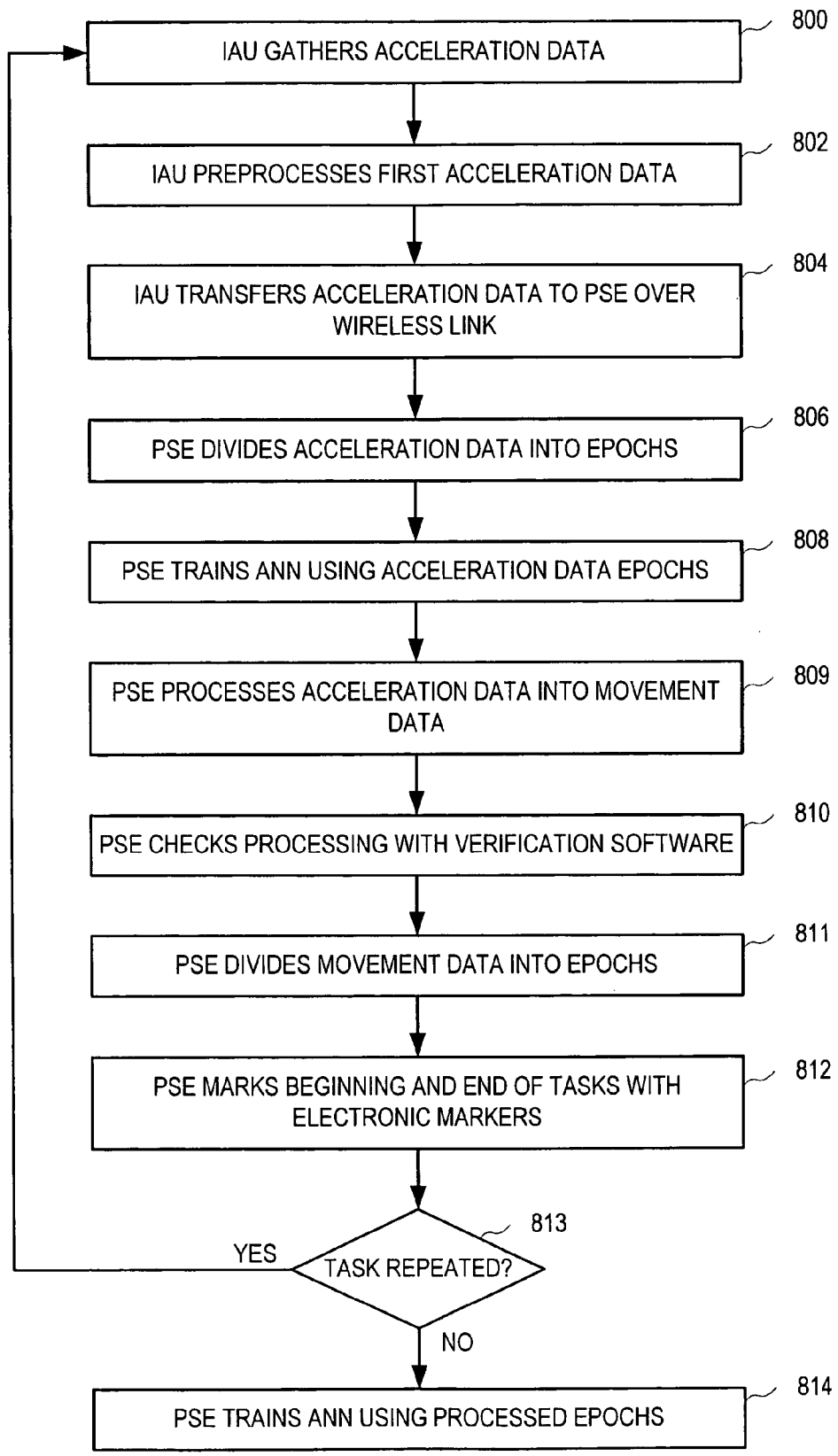
FIGS. 8A-B are flow charts showing one process embodiment for an intelligent wearable monitor system.

FIG. 8A is a flow chart showing an exemplary process for calibrating an intelligent wearable monitor system, i.e., system 700. An IAU (e.g., IAU 104, FIG. 1) gathers acceleration data from a patient, i.e., patient 702, while the patient performs a task or ADL, in step 800. The IAU preprocesses the acceleration data, for example, digitizing the data or adding time and date markers, in step 802, before transferring the acceleration data to a PSE (e.g., PSE 108), i.e., via a wireless link, in step 804. The PSE receives the first acceleration data and divides it into epochs, in step 806. In step 808, the acceleration epochs are used to train an ANN (e.g., ANN 313, FIG. 3). The PSE processes the acceleration data into movement information using linear and non-linear methods in step 809. The PSE may check the processing with verification software in step 810. In step 811, movement information is divided into epochs. The movement information may then be marked, for example with electronic markers placed at the beginning and end of a task, in step 812. Step 813 is a decision. If the task or ADL is repeated, steps 800-813 are repeated. If the ADL is not repeated (decision 813), processed epochs associated with the ADL may be used to further train the ANN, in step 814.

Figure 8B:
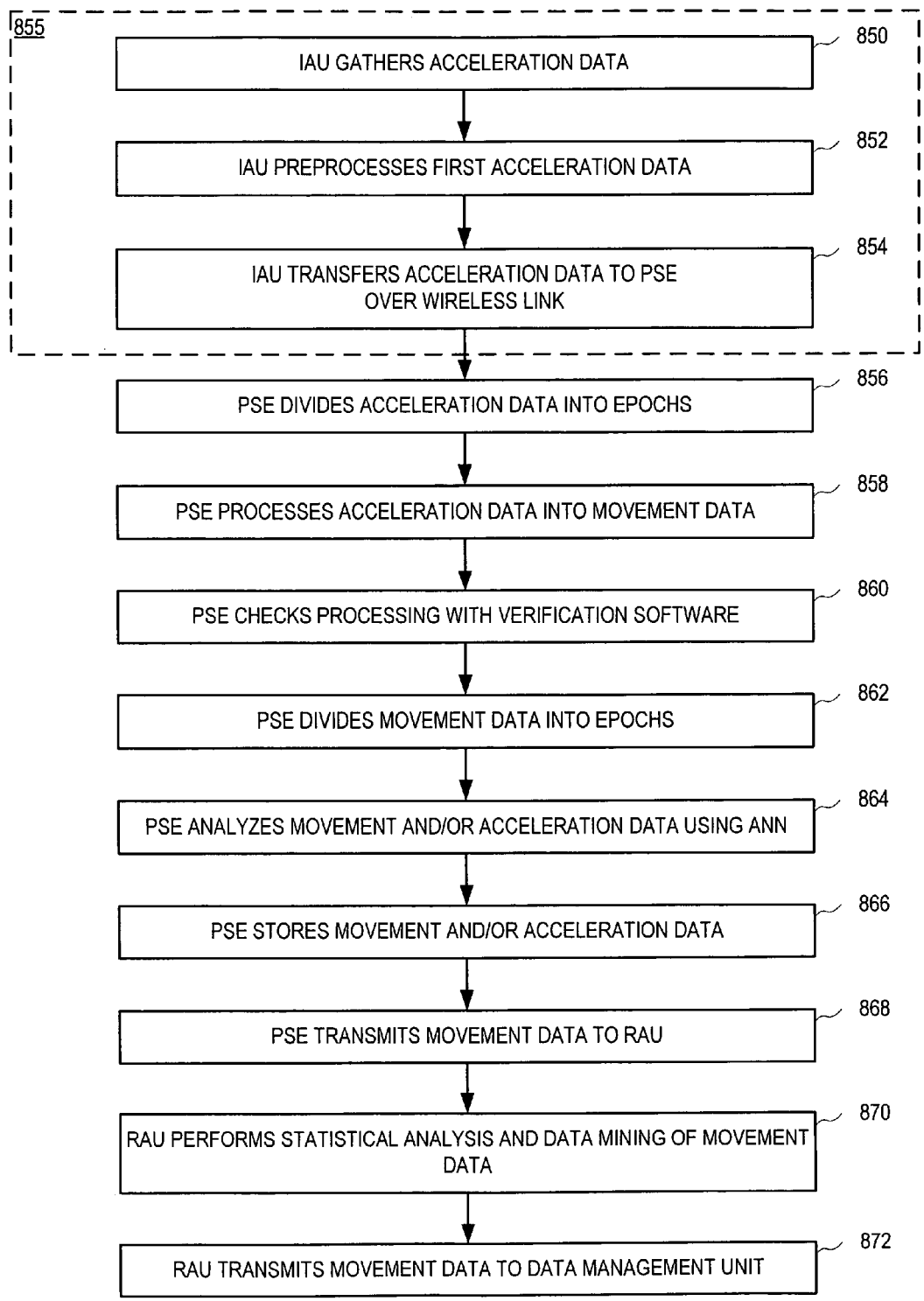

FIG. 8B is a flow chart showing an exemplary process of an intelligent wearable monitor system, i.e., system 700. An IAU (e.g., IAU 104, FIG. 1) gathers acceleration data from a patient, i.e., patient 702, while the patient performs a task or ADL, in step 850. The IAU preprocesses the acceleration data, for example, digitizing the data or adding time and date markers, in step 852, before transferring the acceleration data to a PSE (e.g., PSE 108), i.e., via a wireless link, in step 854. Steps 850, 852 and 854 may repeat as necessary, transferring data from the IAU to the PSE, as shown by dashed box 855. The PSE receives the first acceleration data and divides it into epochs, in step 856. The PSE processes the acceleration data into movement information using linear and non-linear methods in step 858. The PSE may check the processing with verification software in step 860. In step 862, movement information is divided into epochs. In step 864, the PSE analyzes the movement data (and/or its associated acceleration data) using an ANN (e.g., ANN 313, FIG. 3). For example, the PSE may identify the activity responsible for the movement and/or acceleration data by comparing it with acceleration and movement epochs used to train the ANN. Alternately, the PSE may compare the movement and/or acceleration data with a mass ADL index or an existing individualized ADL index. Once the movement information has been analyzed, the PSE may store the movement and/or acceleration data, in step 866. For example, the PSE may store the data in an individualized ADL index. In step 868, the personal server transmits the processed movement information to a remote access unit. The remote access unit may format the data, generating visual representations of the movement information, in step 870. For example, the remote access unit may perform statistical analysis or data mining on the movement information. In step 872, the remote access unit transmits the movement information to a data management unit. Steps 806, 808 and 864 may be performed, for example, as per the methods described in "A neural network approach to monitor motor activities," Sherrill D. M., et al., 2nd Joint Meeting of the IEEE Engineering in Medicine and Biology Society and the Biomedical Engineering Society, Houston, Tex., October 2002, and "Automatic Monitoring of Functional Motor Activities" (M.S. thesis), Sherrill, D. M., Department of Biomedical Engineering, Boston University, Boston, Mass., 2003, incorporated herein by reference.

It is to be understood and appreciated that the above disclosed steps are performed as necessary, and need not be carried out in the order in which they are described.

Figure 9:
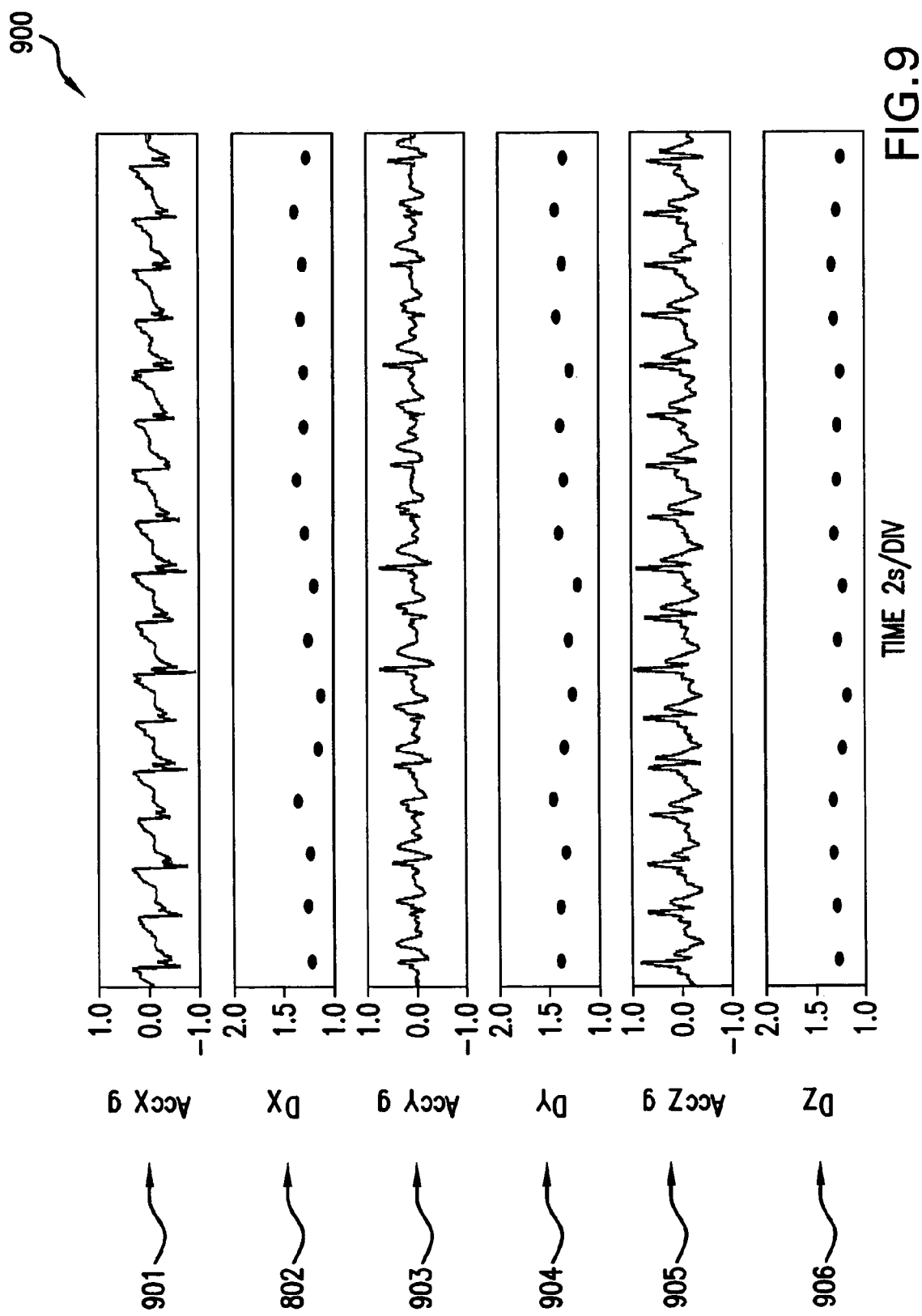
FIG. 9 shows acceleration and fractal dimension data measured in a healthy elderly subject.
Figure 10:
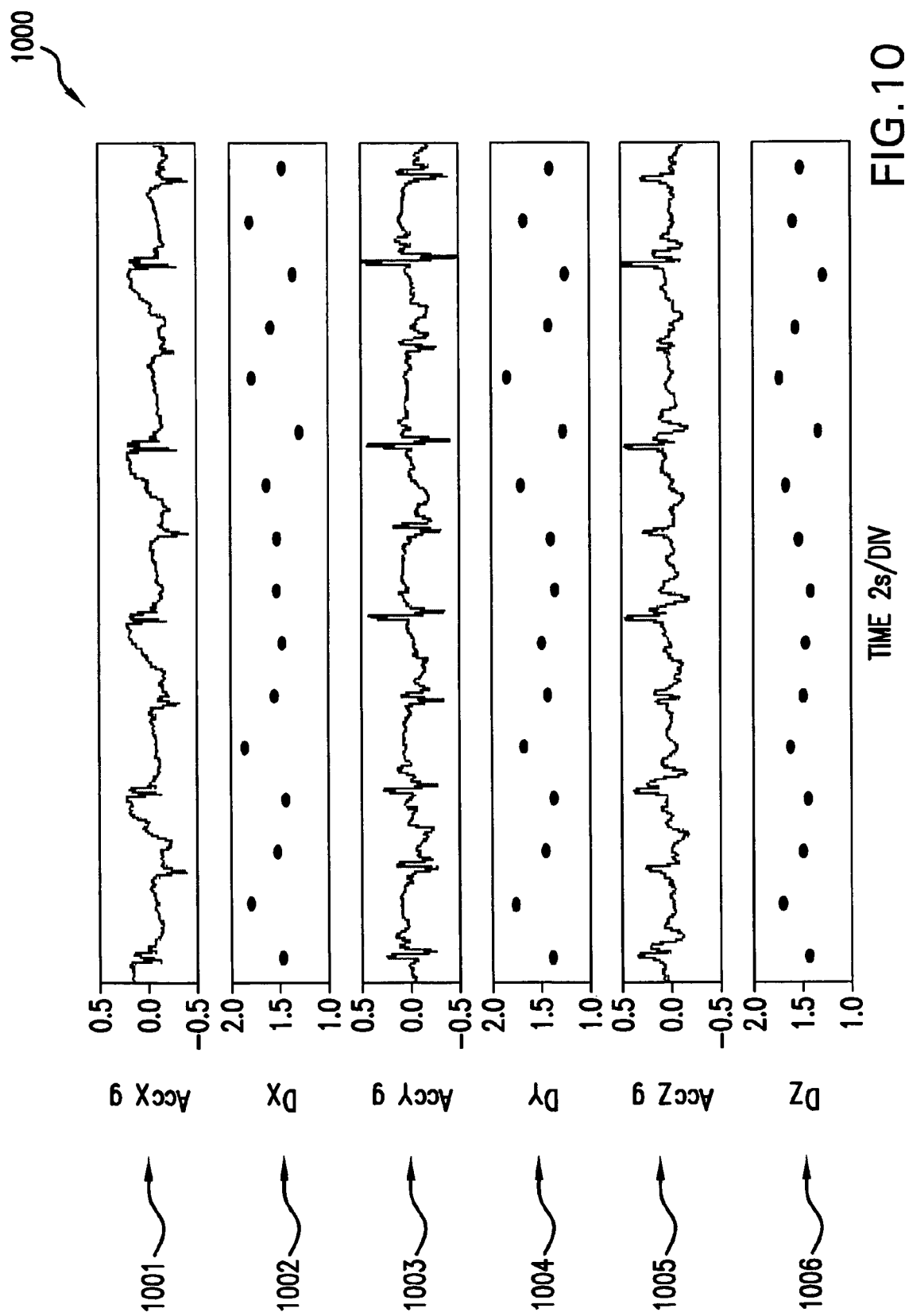
FIG. 10 depicts acceleration and fractal dimension data measured in a post-stroke hemiplegic patient.

Intelligent wearable monitor system 700 may also assess ADL such as walking. FIGS. 9 and 10 show acceleration signals measured during walking, along with the fractal dimensions calculated therefrom, for a healthy elderly subject and a post-stroke hemiplegic patient (Brunnstrom Stage IV), in graphs 900 and 1000, respectively. As can be seen from the Figures, acceleration signals 901, 903 and 905 for the healthy elderly subject have more periodic patterns associated with the step duration in time compared to acceleration signals 1001, 1003 and 1005 of the post-stroke hemiplegic patient. The fractal measures of acceleration signals 1002, 1004 and 1006 of the post-stroke hemiplegic patient are higher than the fractal measures of acceleration 902, 904 and 906 of the healthy elderly subject, and fluctuate more than those of the healthy elderly subject.

Figure 11C:
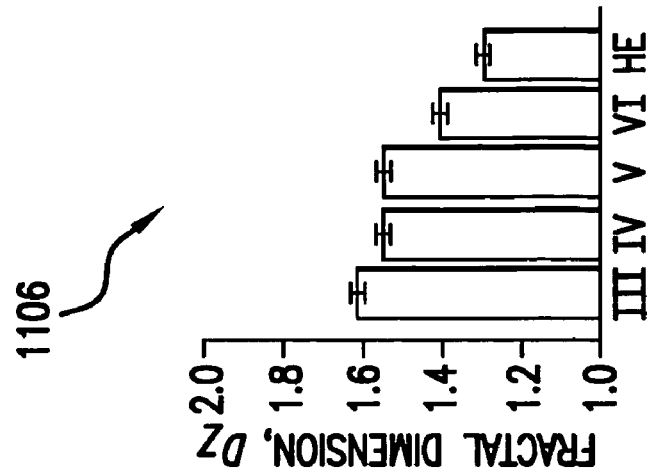
FIGS. 11A-C show three bar graphs depicting differences in fractal values between healthy elderly subjects and post-stroke patients.
Figure 11B:
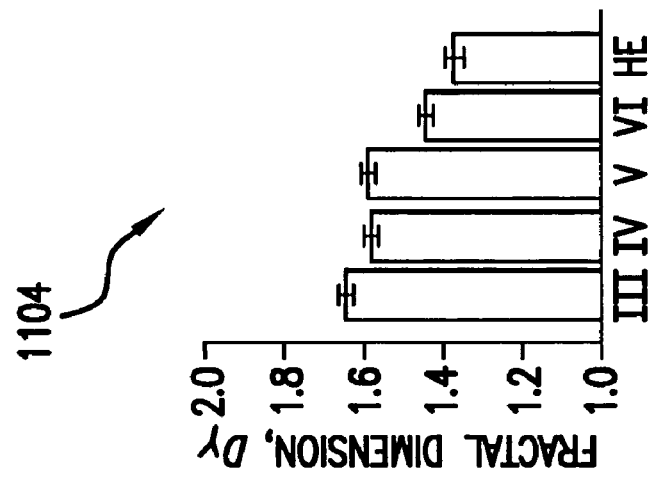
Figure 11A:
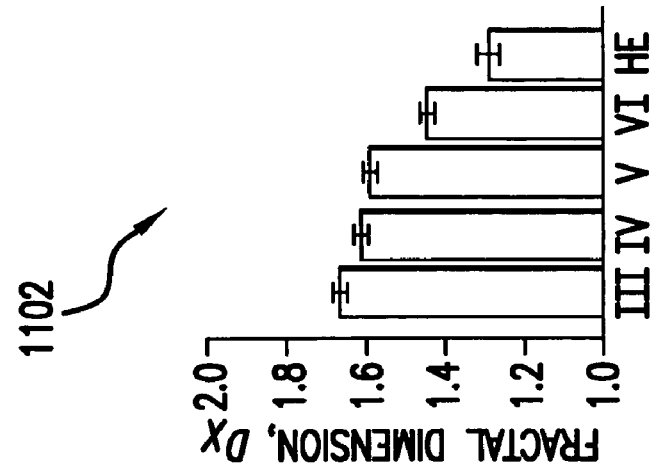

FIGS. 11A-C depict further the difference in fractal values in healthy elderly subjects (HE) and in age-, height- and weight-matched post-stroke patients classified in Brunnstrom stages III, IV, V, VI (differences of age, height and weight between the HE subject and the post-stroke patients were not statistically significant). Bar graphs 1102 (FIG. 11A), 1104 (FIG. 11B) and 1106 (FIG. 11C) show fractal values calculated from acceleration signals in the x (anteroposterior), y (lateral) and z (vertical) directions, respectively. The fractal dimension of acceleration indicates the complexity or smoothness of body motion. For example, the range of the fractal dimension is 1<D<2 for a one-dimensional acceleration signal. A value close to one indicates a smooth signal, and a value close to two indicates a complex (not smooth) signal. Fractal analysis of movement in stroke patients is further described in "Fractal dynamics of body motion in post-stroke hemiplegic patients during walking" (Akay, et al., J. Neural Eng. 1 111-116 (2004)), incorporated herein by reference.

The intelligent wearable monitor system described herein above may provide a useful tool for monitoring a stroke patient outside of the hospital setting. Once initial acceleration data is taken, the wireless personal area network, i.e., WPAN 120, may monitor the patient at home and in the community for un-biased, real-time analysis of ADL.

Intelligent wearable monitor system 100 may track and analyze a patient's motor functions with varying degrees of detail, to aid physicians in diagnosing and/or assessing neurological disorders and their severity. For example, system 100 may aid a physician in diagnosing Parkinson's disease. Parkinson's disease ("PD") is characterized by disabling motor symptoms, including resting tremor, rigidity, akinesia, bradykinesia and a subsequent loss of coordination and balance. Medical treatment of PD often utilizes various dopaminergic drugs (e.g., levodopa), dopamine agonists and electrical stimulation to various basal ganglia structures. These methods of treatment are highly complex, as drug treatment must be adjusted to each patient and often augmented by balancing drugs such as carbidopa to minimize the short-term side effects of levodopa treatment. However, serious side effects including dyskinesia and cognitive and mood disturbance often arise in the long term, thus, drug treatment must be carefully monitored. In one embodiment, intelligent wearable monitor system 100 is used to assess PD and to monitor the efficacy of treatment, and optionally, the appearance and severity of side effects associated with drug treatment.

In one embodiment, patient 102 (e.g., a patient exhibiting motor symptoms such as difficulty in walking) wears IAU 104 and PSE 108 while performing directed ADL in a clinical setting, without the influence of dopamine agonists or dopaminergic drugs such as levodopa. IAU 104 records acceleration data during the directed ADL, for example, during walking. PSE 108 processes the acceleration data into motor function information, as detailed with reference to FIG. 1. For example, PSE 108 may apply the MLE fractal or other nonlinear method to generate movement information. The MLE fractal method and its use in determining fractal dimensions in PD patients are further detailed in "Fractal dynamics of body motion in patients with Parkinson's disease", Sekine et al. (J. Neural Eng. 1 8-15 (2004)), incorporated herein by reference.

The movement information (i.e., fractal dimensions) associated with patient 102's gait may then be viewed by the attending physician at RAU 112 or data management unit 116. The physician may use the movement information to confirm or diagnose Parkinson's and/or its severity. For example, an elevated fractal dimension represents a higher-than-normal complexity of movement, as is characteristic of PD. PD patients have a consistently high fractal dimension to their gait, which appears to increase with the severity of the disease (Sekine, et al.).

FIGS. 12A-C, for example, depict bar graphs 1202 (FIG. 12A), 1204 (FIG. 12B) and 1206 (FIG. 12C) showing the mean value and standard deviation of fractal dimensions for a PD patient 1210 and a healthy elderly subject 1208, calculated from acceleration signals in the x, y and z directions, respectively. Fractal dimensions $D_X$ (graph 1202), $D_Y$ (graph 1204) and $D_Z$ (graph 1206) are consistently and markedly higher in PD patient 1210, and are statistically significant in all acceleration directions: $p<0.01$ in dimensions $D_X$ and $D_Z$ and $p<0.05$ in fractal dimension $D_Y$.

In a further embodiment, intelligent wearable monitor system 100 may be used to monitor and assess the efficacy of Parkinson's treatment. For example, intelligent wearable monitoring system 100 may be calibrated to patient 102, as detailed above, when the patient's system is clear of treatment medications. Patient 102 may then wear intelligent wearable monitor system 102 at home and in the community for a time span, for example, the period of initiation and adjustment of medication. Acceleration data may be recorded by IAU 104, periodically, for example, as ADL are performed before and after medication is taken each day and/or before and after deep brain stimulation. The motor function information generated (i.e., by PSE 104) from such performed ADL may then be compared to motor function information that was obtained during calibration, for the corresponding ADL. Conveniently, because system 100 is a portable, wireless monitor operable to record and transmit accelerometer data for more than one week, ADL measurements may be taken while the patient is at home.

Intelligent wearable monitor system 100 may be used to identify optimal levels of medication. For example, as optimal dosage is reached, the fractal dimensions of the acceleration data (e.g., as shown in FIGS. 12A-B) may decrease, indicating smoother, less complex movement. Intelligent wearable monitor system 100 may also be used to monitor a Parkinson's patient for the appearance and/or severity of drug-related side effects, and to measure the efficacy of different or additional drugs used to combat the side effects. Those skilled in the art will recognize that intelligent wearable monitor system 100 may also be used to monitor drug treatment, rehabilitative therapy or the presence and/or severity of side effects in individuals with other motion-impairing disorders, or injuries.

In yet a further embodiment, intelligent wearable monitor system 100 may determine the physical activities of a patient, to monitor overall activity levels and assess compliance with a prescribed exercise regimen and/or efficacy of a treatment program. System 100 may also measure the quality of movement of the monitored activities. For example, system 100 may be calibrated or trained in the manner previously described, to recognize movements of a prescribed exercise program. Motor function information associated with the recognized movements may be sent to data management unit 116, following processing at PSE 108 and formatting (i.e. generating visual representations) at RAU 112. A physician or clinician with access to data management unit 116 may thus remotely monitor compliance with the prescribed program.

Figure 13:
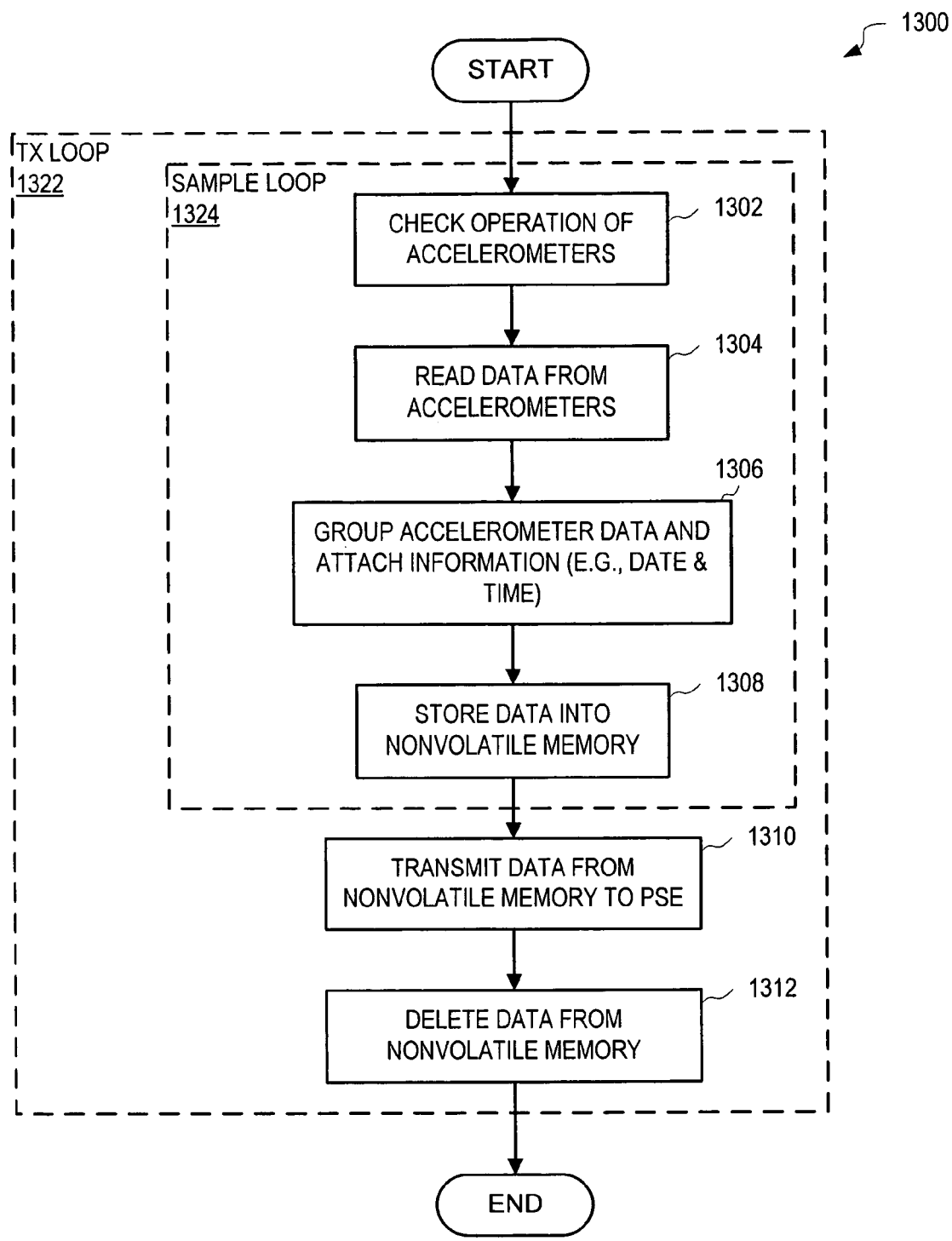
FIG. 13 is a flow chart showing one process embodiment for an intelligent accelerometer unit.

FIG. 13 shows one exemplary process 1300 for acquiring accelerometer data. Process 1300 is, for example, implemented within IAU 104, FIG. 1. In step 1302, process 1300 checks operation of accelerometers. In one example of step 1302, IAU 104 checks a status of accelerometers 204x and 204y to determine correct operation. In step 1304, process 1300 reads accelerometer data from the accelerometers. In one example of step 1304, IAU 104 reads accelerometer data from accelerometers 204x and 204y. In step 1306, process 1300 groups accelerometer data and attaches information (e.g., a data and/or time stamp). In step 1308, process 1300 stores the grouped data into a nonvolatile memory (e.g., memory 203). Steps 1302 through 1308 may repeat, as indicated by the dashed box representing sample loop 1324, to collect additional accelerometer data as necessary.

In step 1310, process 1300 transmits data from the nonvolatile memory to a PSE (e.g., PSE 108, FIG. 1). In step 1312, process 1300 deletes the transmitted data from the nonvolatile memory once transmission is complete. Steps 1302 through 1312 may repeat as necessary to acquire and transfer accelerometer data to the PSE, as indicated by the dotted line representing transmission ("TX") loop 1322.

Figure 14:
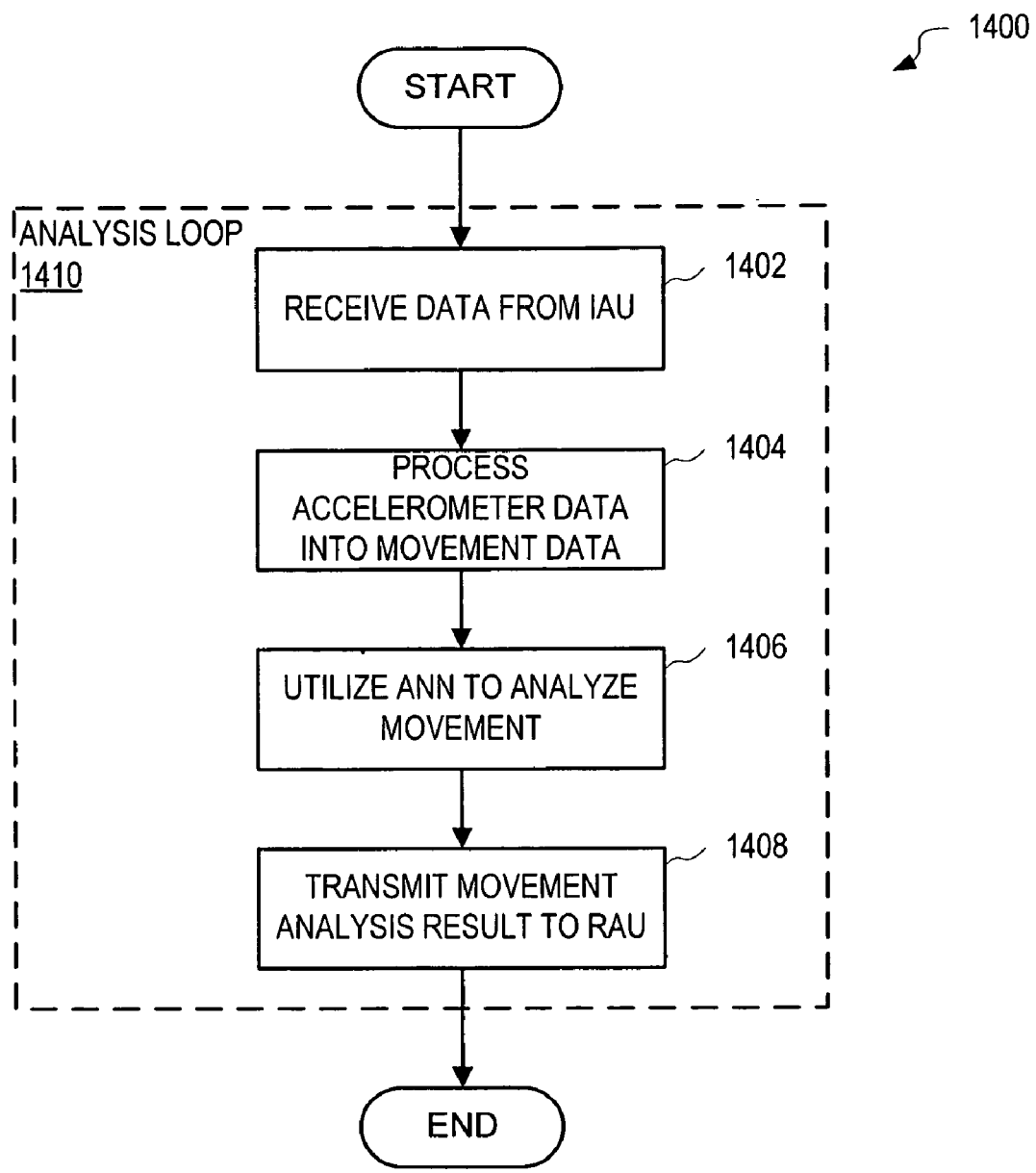
FIG. 14 is a flow chart depicting one process embodiment for a personal server.

FIG. 14 is a flowchart illustrating one exemplary process 1400 for receiving and analyzing accelerometer data from an IAU. Process 1400 is, for example, implemented within PSE 108, FIG. 1. In step 1402, process 1400 receives data from an IAU. In one example of step 1402, PSE 108 receives data from IAU 104 via transceiver 308. In step 1404, process 1400 processes the accelerometer data received in step 1402 into movement data. In step 1406, process 1400 utilizes an ANN to analyze the movement data of step 1404. In one example of step 1406, PSE 108 utilizes ANN 313 to process the movement data of step 1404. In step 1408, process 1400 transmits the movement analysis result to a RAU. In one example of step 1408, PSE 108 transmits, via transceiver 308, results from step 1406 to RAU 112. Steps 1402 through 1408 may repeat, as indicated by dashed box 1410, to receive and analyze additional data from IAU 104.

Figure 15:
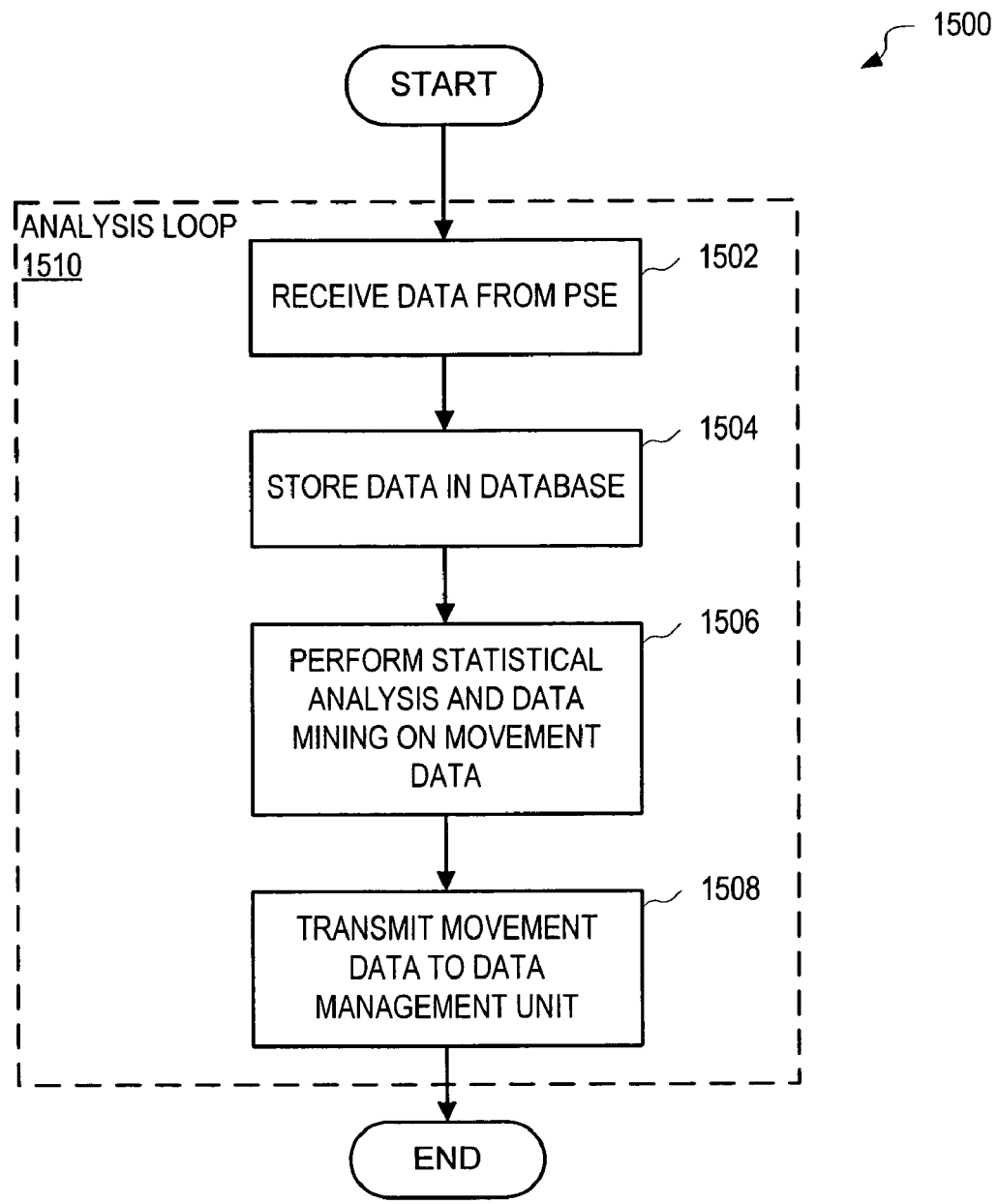
FIG. 15 is a flow chart showing one process embodiment for a remote access unit.

FIG. 15 is a flowchart illustrating one exemplary process 1500 for receiving and storing data transmitted by a PSE. Process 1500 is, for example, implemented within RAU 122, FIG. 1. In step 1502, process 1500 receives data from a PSE. In one example of step 1502, RAU 112 receives data from PSE 108 via transceiver 402. In step 1504, process 1500 stores the data, received in step 1502, in a database. In one example of step 1504, RAU 112 stores data received from PSE 108 in database 412. In step 1506, process 1500 performs statistical analysis and data mining on the movement data stored in the database. In one example of step 1506, RAU 112 utilizes analysis tools 410 and data mining 408 of software 406 to perform statistical analysis and data mining on database 412. In step 1508, process 1500 transmits the data to a data management unit. In one example of step 1508, RAU 112 transmits, via transceiver 402, movement data to data management unit 116, FIG. 1, via a link 114.

Certain embodiments of the intelligent wearable monitor system include additional features. For example, in one embodiment intelligent wearable monitor system 100 contains more than one IAU (e.g., IAU 104) linked to a single PSE (e.g., PSE 108). In another example, an IAU may contain additional sensors such as temperature sensors or galvanic skin response sensors. In one embodiment, PSE 108 initiates measurement of acceleration data by IAU 104.

Results

The intelligent wearable monitor system 100 was tested to detect motor activity, for example falling events. An intelligent accelerometer unit (i.e., IAU 104) with four channels of ACC capacity at 40 Hz was mounted on a vertical rotating disk such that the tested axis rotated vertically covering the range −g to +g. A group of volunteers were fitted with the IAU and performed several physical activities while wearing the IAU. We evaluated both false impacts and false non-impacts. The IAU was programmed with a set of default threshold values associated with a fall detection algorithm. The outcomes obtained for the default parameters were compared with the outcomes obtained for a set of optimal parameters dependent on the anthropometric characteristics of each subject and the type of environment (i.e., the floor). The corresponding amplitude threshold was (mean±SD) 120±9 on hard floor and 117±12 on soft floor. The energy threshold was 19±10 in hard floor and 10±5 in soft floor. In the study, all fall events were correctly detected. Details of this study were published in "Preliminary evaluation of a full-time falling monitor for the elderly" (A. Diaz et al., 26th Int'l Conf. IEEE Engineering in Medicine and Biology Society, San Francisco, Calif., 2004), incorporated herein by reference.

Intelligent wearable monitor system 100 was also tested to outline linear and nonlinear features of acceleration data measured in patients of differing motor ability. Two stroke patients and a healthy subject, i.e., patients A and B, and the healthy elderly subject (HE) discussed above with respect to FIGS. 5A-5C and 6A-6B participated in the pilot study.

Subjects wore an array of acceleration sensors. Sensors were placed on the affected side for the stroke subjects and on the dominant side for the control subject. Six channels of acceleration data were recorded using two triaxial sensor configurations applied to the lateral aspect of upper and lower arm, approximately 10 cm above and 10 cm below the elbow joint center. Acceleration signals were digitized at 128 Hz. Subjects were positioned according to the standards of the Wolf Motor Function test and acceleration data was recorded while the subjects performed three to five repetitions of the following 15 Wolf Motor Function tasks:

placing the forearm on a table from the side ("forearm to table");

moving the forearm from the table to a box on the table from the side ("forearm to box");

extending the elbow to the side ("extend elbow");

extending the elbow to the side against a light weight ("extend elbow with weight");

placing the hand on a table from the front ("hand to table");

moving the hand from table to box ("hand to box");

flexing the elbow to retrieve a light weight ("reach and retrieve");

lifting a can of soda;

lifting a pencil, lifting a paper clip;

stacking checkers, flipping cards;

turning a key in a lock;

folding a towel, and lifting a basket from the table to a shelf above the table.

All tasks were performed from a seated position except basket lifting, which was performed while standing. Before each task, the experimenter described the movements and gave a demonstration of the task. The subjects then rehearsed the motion prior to the recording. Contrary to the Wolf Motor Function test, which strives to avoid practice effects, our test was aimed at measuring each subject's best QOM. Subjects were allowed to practice to ensure their best performance of each task during recording of movement.

As shown in FIGS. 5A-5C and 6A-6B, differences in movement pattern characteristics were detected by means of acceleration measurements from recordings of functional motor tasks (FMT). Both linear and nonlinear features calculated from the acceleration data showed differences in QOM between patients A and B, and between the patients and the HE control subject.

Changes may be made in the intelligent wearable monitor system described herein without departing from the scope thereof. It should thus be noted that the matter contained in the above description or shown in the accompanying drawings should be interpreted as illustrative and not in a limiting sense. The following claims are intended to cover all generic and specific features described herein, as well as all statements of the scope of the present system and methods, which, as a matter of language, might be said to fall therebetween.

What is claimed is:

1. A method of monitoring the motor function of a patient, comprising:

capturing acceleration data from the patient with at least a first accelerometer and a second, biaxial accelerometer located on an appendage of the patient, the first accelerometer capturing objective acceleration data, and the second, biaxial accelerometer capturing subjective acceleration data relative to at least the first accelerometer;

wirelessly communicating the acceleration data to a personal server positioned on the patient at a location spaced from the accelerometers; and processing the acceleration data by computing nonlinear parameters for the acceleration data to generate at least two levels of motor function information, the nonlinear parameters chosen from the group of a maximum likelihood estimator fractal, an approximate cross entropy method, and an average amount of mutual information measure.

2. The method of claim 1, further comprising formatting the motor function information by performing at least one of statistical analysis and data mining.

3. The method of claim 1, further comprising wirelessly transmitting the motor function information to a remote access unit, the remote access unit having one or more of a user interface, a transceiver, a processor and a non-volatile memory.

4. The method of claim 1, wherein capturing acceleration data from the patient comprises recording and preprocessing the acceleration data from the accelerometers with a microprocessor configured with the accelerometers in an intelligent accelerometer unit.

5. The method of claim 3, further comprising performing at least one of statistical analysis and data mining to format the motor function information into formatted information at the remote access unit.

6. The method of claim 5, further comprising wirelessly transmitting the formatted information to a data management unit, for one or both of storage and analysis.

7. The method of claim 6, further comprising:

displaying the formatted information at the data management unit; and determining a level of functional impairment of the patient.

8. The method of claim 1, processing the acceleration data comprising one or more of:

dividing the acceleration data into epochs;

electronically marking the epochs;

attaching the time and date to the acceleration data, and identifying and measuring physical activity.

9. The method of claim 1, the step of processing the acceleration data further comprising processing, identifying and measuring physical activity.

10. The method of claim 9, the step of processing the acceleration data further comprising assessing changes in the patient's motor function.

11. The method of claim 1, the step of processing comprising processing at the personal server.

12. The method of claim 1, further comprising transmitting the motor function information to a remote access unit and performing data mining and analysis at the remote access unit, to format the motor function information.

13. The method of claim 12, further comprising wirelessly transmitting the formatted information to a data management unit.

14. The method of claim 13, further comprising displaying the formatted information at the data management unit.

15. The method of claim 14, further comprising determining a level of functional impairment of the patient.

16. The method of claim 15, wherein determining a level of functional impairment of the patient comprises one or both of diagnosing a neurological disorder and determining the severity of a neurological disorder.

* * * * *

UNITED STATES PATENT AND TRADEMARK OFFICE
CERTIFICATE OF CORRECTION

| | | |
|---|---|---|
| PATENT NO. | : 7,981,058 B2 | Page 1 of 1 |
| APPLICATION NO. | : 11/079496 | |
| DATED | : July 19, 2011 | |
| INVENTOR(S) | : Metin Akay | |

It is certified that error appears in the above-identified patent and that said Letters Patent is hereby corrected as shown below:

IN THE SPECIFICATIONS:

Column 3, Line 11, "wearer example" should read --wearer, for example--.

Signed and Sealed this
Thirteenth Day of September, 2011

David J. Kappos
*Director of the United States Patent and Trademark Office*